(54) STN LIQUID-CRYSTAL DISPLAY

(75) Inventors: Harald Hirschmann, Darmstadt; Sven Schüpfer, Aschaffenburg; Marcus Reuter, Darmstadt; Volker Reiffenrath, Rossdorf; Sabine Schoen, Darmstadt, all of (DE)

(73) Assignee: Merck Patent Gesellschaft, Darmstadt (DE)

( * ) Notice: Under 35 U.S.C. 154(b), the term of this patent shall be extended for 0 days.

This patent is subject to a terminal disclaimer.

(21) Appl. No.: 09/200,463

(22) Filed: Nov. 27, 1998

(30) Foreign Application Priority Data

Nov. 28, 1997 (DE) .............................................. 197 52 951

(51) Int. Cl.[7] .......................... C09K 19/34; C09K 19/30; C09K 19/20; G02F 1/1333

(52) U.S. Cl. ................ 428/1.1; 252/299.01; 252/299.61; 252/299.63; 252/299.66; 252/299.67; 349/186

(58) Field of Search .......................... 252/299.01, 299.61, 252/299.63, 299.66, 299.67; 349/182, 186; 428/1.1

(56) References Cited

U.S. PATENT DOCUMENTS

| | | | |
|---|---|---|---|
| 5,702,640 | * 12/1997 | Junge et al. | 252/299.01 |
| 5,714,087 | * 2/1998 | Pausch et al. | 252/299.01 |
| 5,772,914 | * 6/1998 | Pauluth et al. | 252/299.6 |
| 5,976,404 | * 11/1999 | Hirschmann et al. | 252/299.01 |
| 5,997,767 | * 12/1999 | Hirschmann et al. | 252/299.63 |
| 6,028,655 | * 2/2000 | Weber et al. | 349/182 |
| 6,054,193 | * 4/2000 | Hirschmann et al. | 428/1.1 |
| 6,056,894 | * 5/2000 | Hirschmann et al. | 252/299.63 |
| 6,063,456 | * 5/2000 | Hirschmann et al. | 428/1.1 |
| 6,080,451 | * 6/2000 | Hirschmann et al. | 428/1.1 |

* cited by examiner

*Primary Examiner*—Shean C. Wu
(74) *Attorney, Agent, or Firm*—Millen White Zelano & Branigan

(57) ABSTRACT

Supertwist liquid-crystal displays (SLCDs) with outstanding properties are obtained if the nematic liquid-crystal mixtures used therein comprise one or more compounds of the formula IA

IA

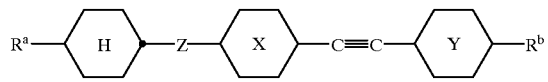

and one or more compounds of the formula IB

IB

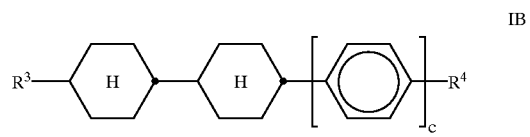

$R^a$ is alkyl, alkoxy, alkenyl or alkenyloxy having 1 to 12 carbon atoms, $R^b$ is alkyl or alkoxy having 1 to 5 carbon atoms, Z is —COO —CH$_2$CH$_2$— or a single bond, and

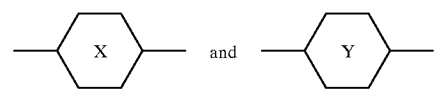

are each, independently of one another,

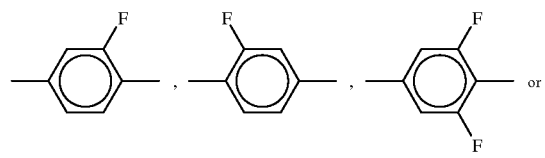

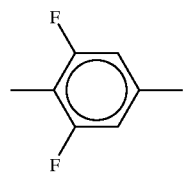

and one of the rings

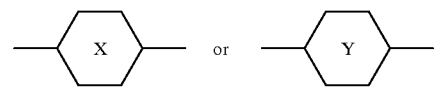

may alternatively be

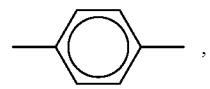

$R^3$ is an alkenyl group having 2 to 7 carbon atoms, $R^4$ is as defined for $R^a$ in the formula IA, and c is 0 or 1.

19 Claims, No Drawings

STN LIQUID-CRYSTAL DISPLAY

The invention relates to supertwist liquid-crystal displays (SLCDs) or supertwisted nematic (STN) displays having very short response times and good steepnesses and angle dependencies, and to the new nematic liquid-crystal mixtures used therein.

BACKGROUND OF THE INVENTION

SLCDs as defined in the preamble are known, for example from EP 0 131 216 B1; DE 34 23 993 A1; EP 0 098 070 A2; M. Schadt and F. Leenhouts, 17th Freiburg Congress on Liquid Crystals (8.–10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784–L 1786 (1987); F. Leenhouts et al., Appl. Phys. Lett. 50 (21), 1468 (1987); H. A. van Sprang and H. G. Koopman, J. Arpl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987) and E. P. Raynes, Mol. Cryst. Liq. Cryst. Letters Vol. 4 (1), pp. 1–8 (1986). The term SLCD here covers any more highly twisted display element with a value for the twist angle of between 160° and 360°, such as, for example, the display elements of Waters et al. (C. M. Waters et al., Proc. Soc. Inf. Disp. (New York) (1985) (3rd Intern. Display Conference, Kobe, Japan), STN-LCDs (DE-A 35 03 259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236, DST-LCDs (EP-A 0 246 842) or BW-STN-LCDs (K. Kawasaki et al., SID 87 Digest 391 (20.6)).

SLCDs of this type are distinguished, in comparison to standard TN displays, by significantly better steepnesses of the electrooptical characteristic line and consequently better contrast values, and by significantly less angle dependence of the contrast. Of particular interest are SLCDs having very short response times, in particular also at relatively low temperatures. In order to achieve short response times, the rotational viscosities of the liquid-crystal mixtures were hitherto optimized using usually monotropic additives having relatively high vapor pressure. However, the response times achieved were not adequate for all applications.

In order to achieve a steep electrooptical characteristic line in SLCDs, the liquid-crystal mixtures should have relatively large values for $K_{33}/K_{11}$ and relatively small values for $\Delta\epsilon/\epsilon_{195}$.

In addition to optimization of the contrast and the response times, further important requirements are made of mixtures of this type:
1. A broad d/p window
2. High long-term chemical stability
3. High electrical resistance
4. Low frequency and temperature dependence of the threshold voltage.

The parameter combinations achieved are still far from adequate, in particular for high-multiplex, but also for low- and medium-multiplex STNs (1/400). This is in some cases attributable to the fact that the various requirements are affected in opposite manners by material parameters.

There thus continues to be a great demand for SLCDs, in particular for high-resolution displays (XGA), having very short response times and at the same time a large operating temperature range, high characteristic line steepness, good angle dependence of the contrast and low threshold voltage which meet the abovementioned requirements.

SUMMARY OF THE INVENTION

The invention has an object of providing SLCDs which do not have the above-mentioned disadvantages, or only do so to a lesser extent.

Upon further study of the specification and appended claims, further objects and advantages of this invention will become apparent to those skilled in the art.

It has now been found that the objects can be achieved if nematic liquid-crystal mixtures are used which comprise one or more compounds of the formula IA

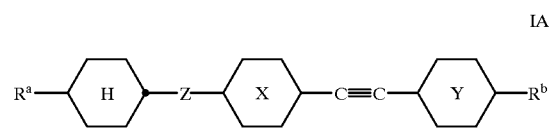

in which $R^a$ is alkyl, alkoxy, alkenyl or alkenyloxy having 1 to 12 carbon atoms, $R^b$ is alkyl or alkoxy having 1 to 5 carbon atoms, Z is —COO—, —CH$_2$CH$_2$— or a single bond, and

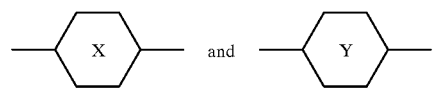

are each, independently of one another,

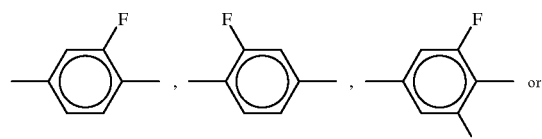

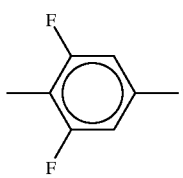

and one of the rings

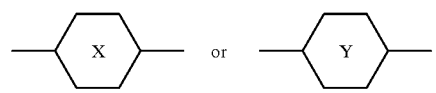

may alternatively be

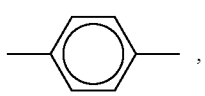

and one or more compounds of the formula IB

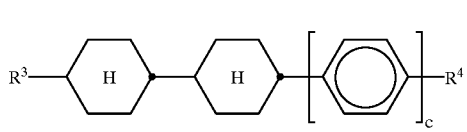

in which
R³ is an alkenyl group having 2 to 7 carbon atoms,
R⁴ is as defined for $R^a$ in the formula IA, and
c is 0 or 1.

The use of compounds of the formulae IA and IB in the mixtures for SLCDs according to the invention produces, for example, long shelf lives in the display at low temperatures. These shelf lives are, for example, longer than in the case of the use of analogous liquid-crystal mixtures which comprise corresponding non-fluorinated tolane compounds instead of the compounds of the formula IA.

Furthermore, the mixtures according to the invention are distinguished by the following advantages:
they have low viscosity,
they have low temperature dependence of the threshold voltage and the operating voltage.

The invention also relates to a liquid-crystal display containing
two outer plates which, together with a frame, form a cell,
electrode layers with alignment layers on the insides of the outer plates,
a pretilt angle between the longitudinal axis of the molecules at the surface of the outer plates and the outer plates of from about 1 degree to 30 degrees, and
a twist angle of the liquid-crystal mixture in the cell from alignment layer to alignment layer with a value of between 100° and 600°, and
a nematic liquid-crystal mixture of positive dielectric anisotropy which is present in the cell, consisting of
a) 5–90% by weight of a liquid-crystalline component A consisting of one or more compounds having a dielectric anisotropy of greater than +1.5;
b) 10–80% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5; and
d) an optically active component C in such an amount that the ratio between the layer thickness (separation of the outer plates) and the natural pitch of the chiral nematic liquid-crystal mixture is from about 0.2 to 1.3,
characterized in that the liquid-crystal mixture comprises one or more compounds of the formula IA

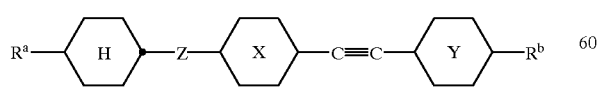

in which
$R^a$ is alkyl, alkoxy, alkenyl or alkenyloxy having 1 to 12 carbon atoms,
$R^b$ is alkyl or alkoxy having 1 to 5 carbon atoms, Z is —COO—, —CH₂CH₂— or a single bond, and

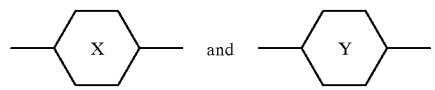

are each, independently of one another,

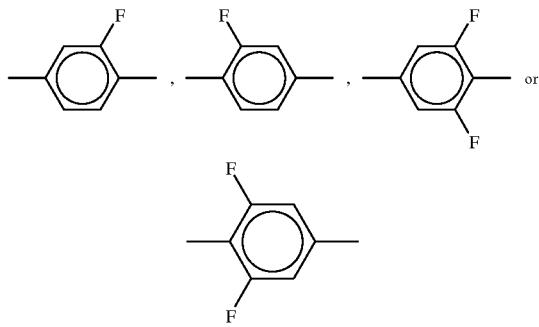

and one of the rings

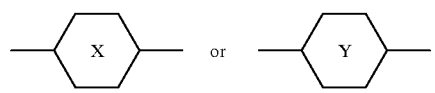

may alternatively be

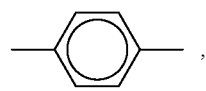

and component B comprises one or more compounds of the formula IB

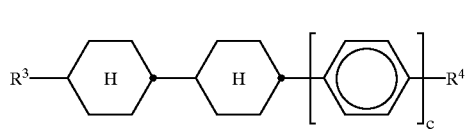

in which
R³ is an alkenyl group having 2 to 7 carbon atoms,
R⁴ is as defined for Ra in the formula IA, and
c is 0 or 1.

The invention also relates to corresponding liquid-crystal mixtures for use in SLCDs.

Preferred compounds of the formula IA are those compounds in which Z is a single bond.

Particularly preferred compounds of the formula IA are the compounds of the subformulae IA1 to IA10

IA1

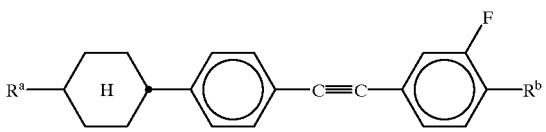

IA2
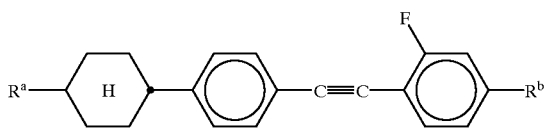

IA3
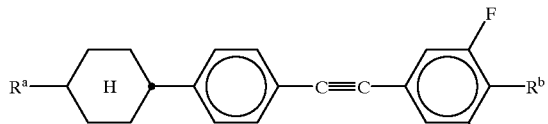

IA4
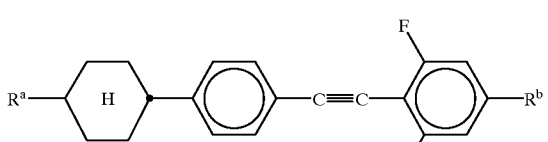

IA5
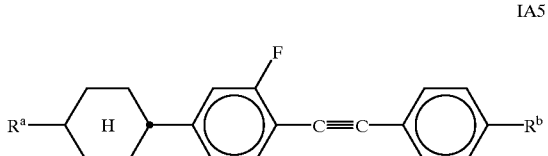

IA6
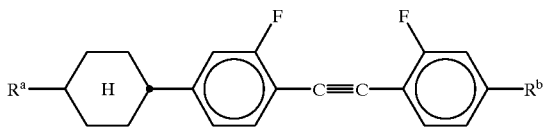

IA7
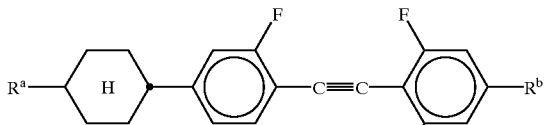

IA8
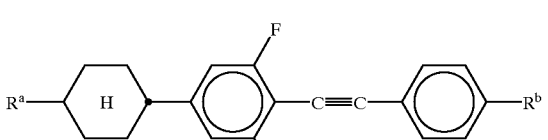

IA9
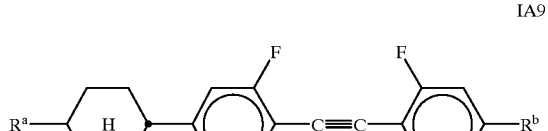

IA10
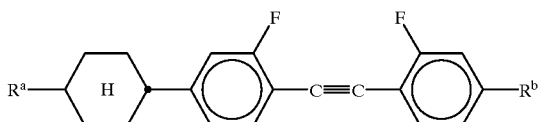

in which $R^a$ and $R^b$ are each, independently of one another, as defined under the formula IA and are preferably each, independently of one another, straight-chain alkyl or alkoxy having 1 to 5 carbon atoms, vinyl or straight-chain 1E- or 3E-alkenyl having 3 to 7 carbon atoms, in particular $R^a$ is straight-chain alkyl having 1 to 5 carbon atoms, vinyl or straight-chain 1E- or 3E-alkenyl having 3 to 7 carbon atoms, and $R^b$ is straight-chain alkyl having 1 to 5 carbon atoms.

Of the particularly preferred compounds of the formulae IA1 to IA10, particular preference is given to those compounds in which

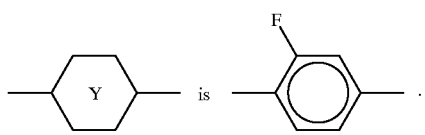

Particular preference is furthermore given to those compounds in which

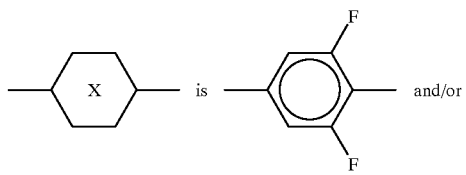 and/or

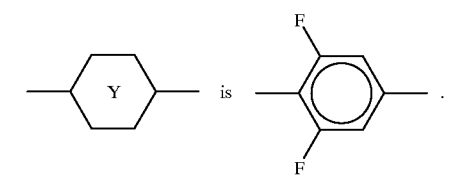

From the group of compounds of the formulae IA1 to IA10, the compounds of the formulae IA2, IA4, IA8 and IA10 are very especially preferred.

The formula IB embraces the following compounds

IB1
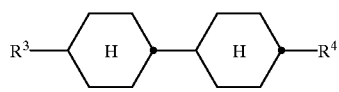

IB2
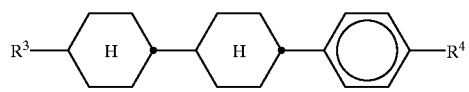

in which $R^3$ is an alkenyl group having 2 to 7 carbon atoms, and $R^4$ is as defined for $R^a$ in the formula IA. Preference is given to compounds of the formulae IB1 and IB2 in which $R^3$ is a vinyl or 1E- or 3E-alkenyl having 3 to 7 carbon atoms and $R^4$ is as defined for Ra in the formula IA.

Particularly preferred compounds of the formula IB1 are those of the subformulae IB1-1 to IB1-5.

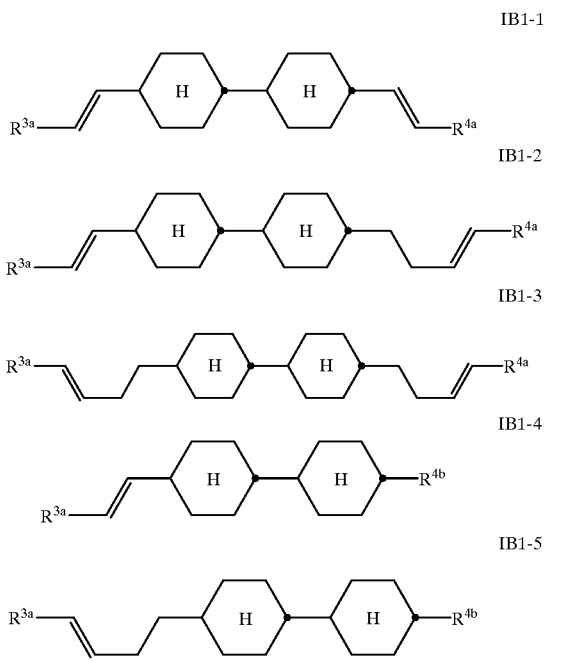

in which $R^{3a}$ and $R^{4a}$ are each, independently of one another, H, $CH_3$, $C_2H_5$ or $n\text{-}C_3H_7$ and $R^{4b}$ is n-alkyl having 1 to 8 carbon atoms.

Particularly preferred compounds of the formula IB2 are those of the subformulae IB2-1 and IB2-2

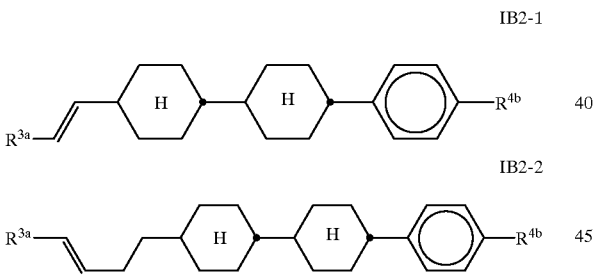

in which $R^{3a}$ and $R^{4b}$ are each, independently of one another, as defined under the compounds of the formulae IB1-1 to IB1-5.

Particular preference is given to liquid-crystal displays according to the invention in which component B comprises at least one compound selected from the formulae IB1-4, IB2-1 and IB2-2.

Component A preferably comprises one and more compounds of the formulae II and/or III

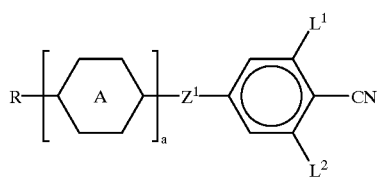

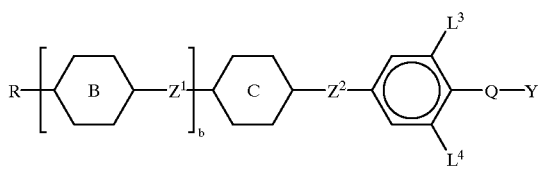

in which

R is an alkyl, alkoxy or alkenyl group having 1 to 12 carbon atoms, in which, in addition, one or two non-adjacent $CH_2$ groups may be replaced by —O—, —CH=CH—, —CO—, —OCO— or —COO—, in such a way that O atoms are not linked directly to one another,

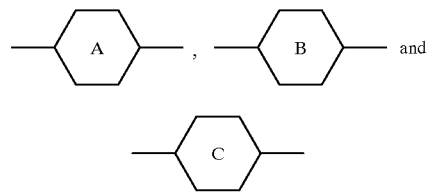

are each, independently of one another,

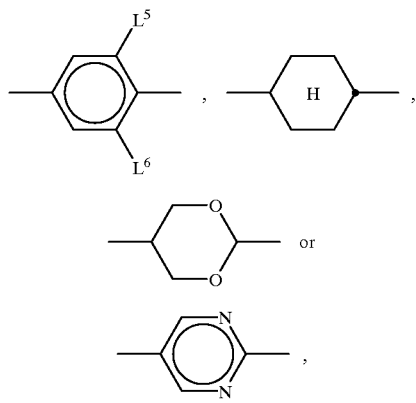

$L^1$ to $L^6$ are each, independently of one another, H or F, $Z^1$ is —COO—, —$CH_2CH_2$— or a single bond, $Z^2$ is —$CH_2CH_2$—, —COO—, —C≡C— or a single bond, Q is —$CF_2$—, —CHF—, —$CH_2$—, —$OCF_2$—, —OCHF— or a single bond, Y is F or Cl a is 1 or 2, and b is 0 or 1.

Preferred compounds of the formula II conform to the subformulae IIa to IIh:

IIa
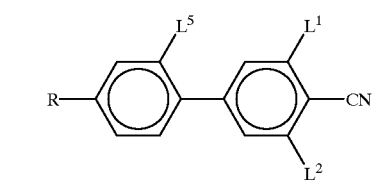

IIb
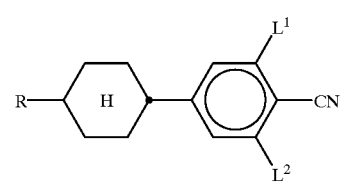

IIc
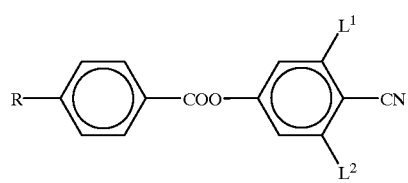

IId
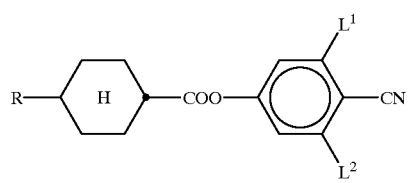

IIe
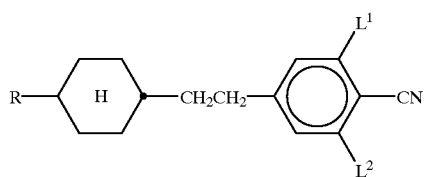

IIf
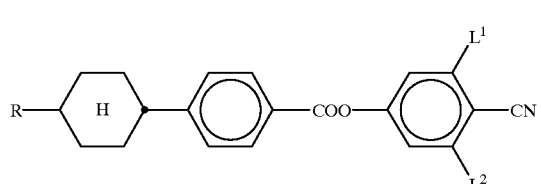

IIg
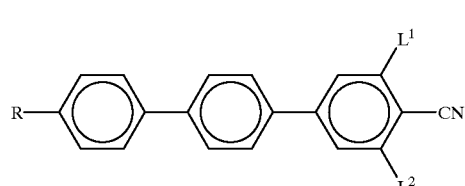

IIh
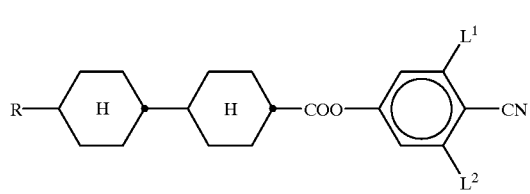

in which R, $L^1$, $L^2$ and $L^5$ are as defined under the formula II.

Of the compounds of the formulae IIa to IIh, preference is given to those of the formulae IIa, IIb, IIc and IIf. Particular preference is given to mixtures which comprise one or more compounds of the following subformulae:

IIb1
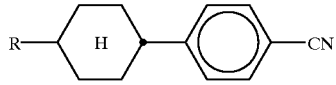

IIb2
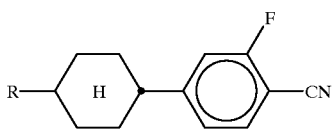

IIb3

IIc1
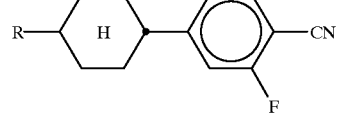

IIc2
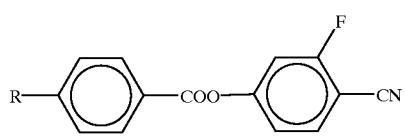

IIf1
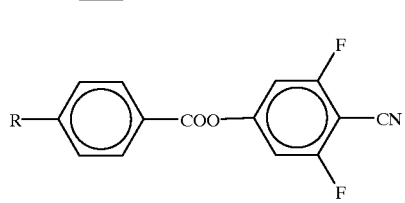

IIf2
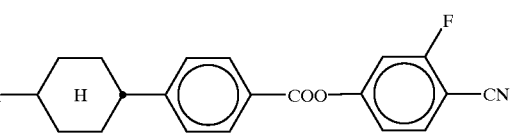

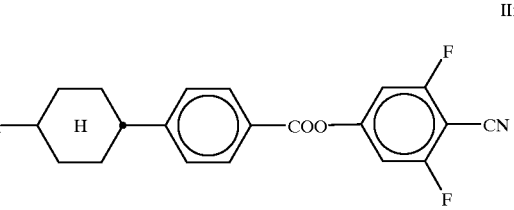

in which R is as defined under the formula II.

In a particularly preferred embodiment, component A additionally comprises compounds of the formulae AI to AIV:

AI
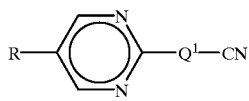

-continued

AII
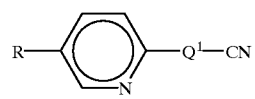

AIII
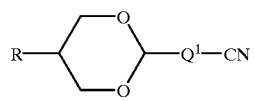

AIV
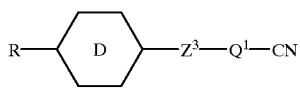

in which

R is an alkyl, alkoxy or alkenyl group having 1 to 12 carbon atoms, in which, in addition, one or two non-adjacent CH$_2$ groups may also be replaced by —O—, —CH=CH—, —CO—, —OCO— or —COO—, in such a way that O atoms are not linked directly to one another

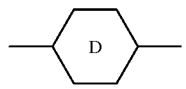

and Q$^1$ are each, independently of one another,

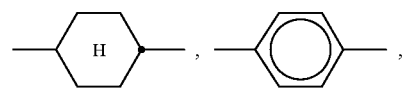

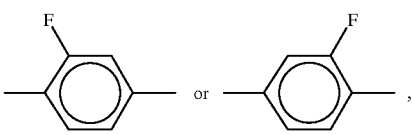

and
Z$^3$ is

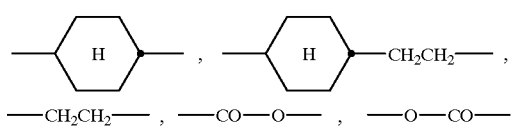

—CH$_2$CH$_2$—, —CO—O—, —O—CO— or a single bond

The mixtures according to the invention preferably comprise one or more polar compounds having a high clearing point selected from the group consisting of the compounds AIV1 to AIV4:

AIV1
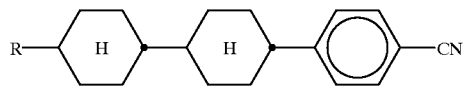

-continued

AIV2
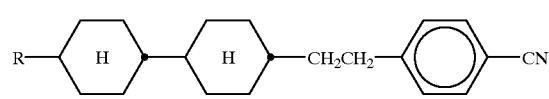

AIV3
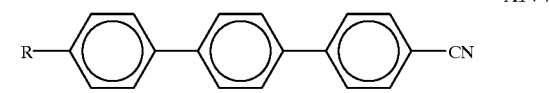

AIV4

in which R is as defined under the formulae AI to AIV.

In the compounds AIV1 to AIV4, the 1,4-phenylene rings can also be laterally substituted by one or two fluorine atoms. Preferred compounds of this type are the compounds of the formulae AIV1-1, AIV1-2 and AIV1-3:

AIV1-1
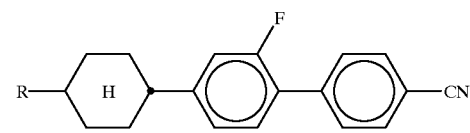

AIV1-2
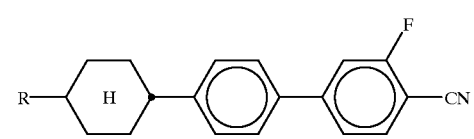

AIV1-3
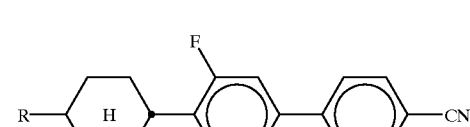

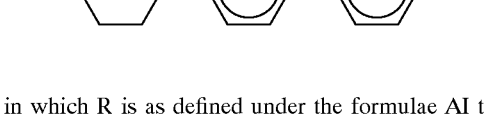

in which R is as defined under the formulae AI to AIV.

In the mixtures according to the invention which comprise compounds of the formulae AIV1 to AIV4, the proportion of these compounds I is preferably from about 2 to 25%.

Preferred compounds of the formula III conform to the subformulae IIIa–IIIv:

IIIa
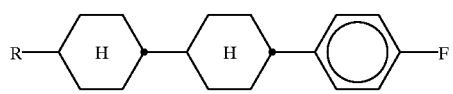

IIIb
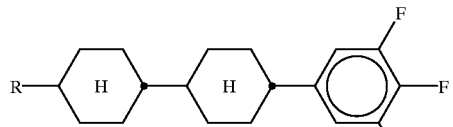

IIIc
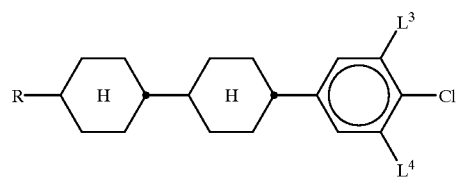
IIId
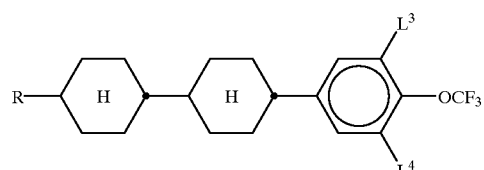
IIIe
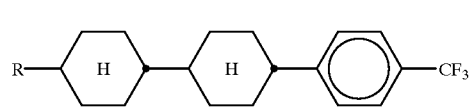
IIIf
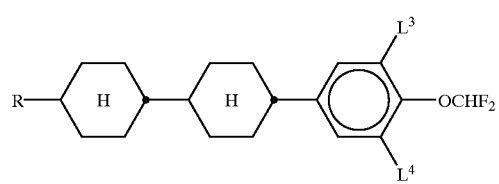
IIIg
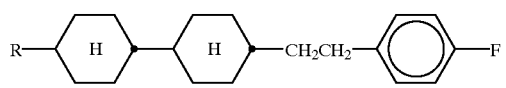
IIIh
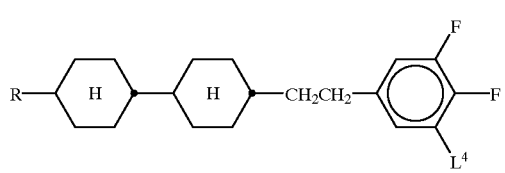
IIIi
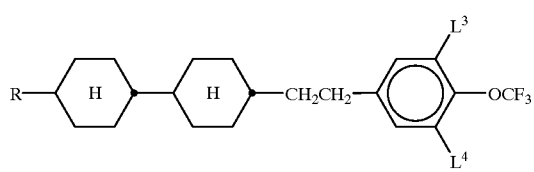
IIIj
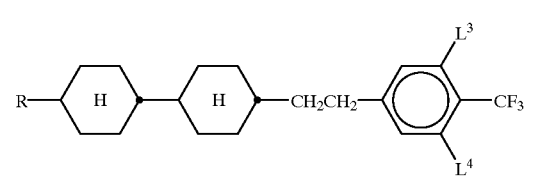
IIIk
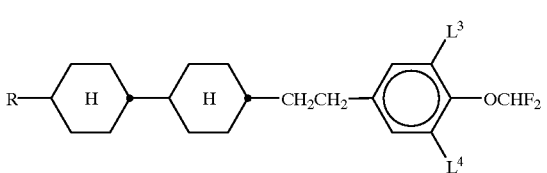
IIIm
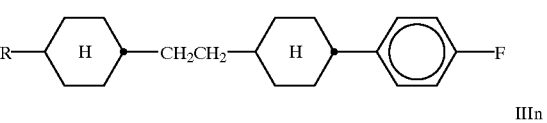
IIIn
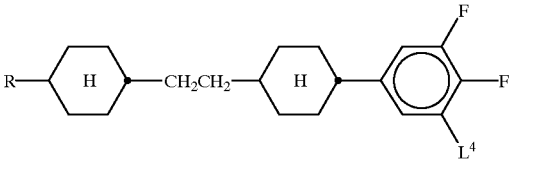
IIIo
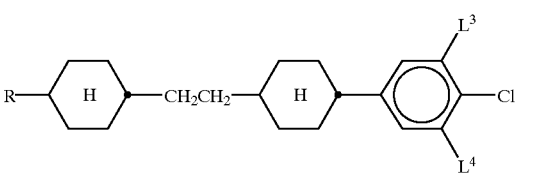
IIIp
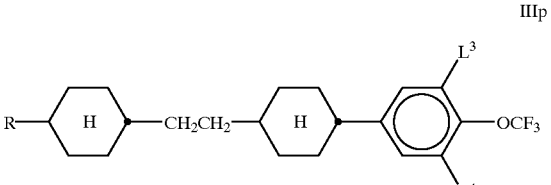
IIIq
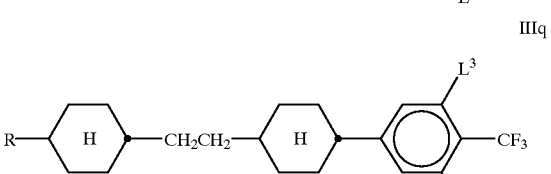
IIIr
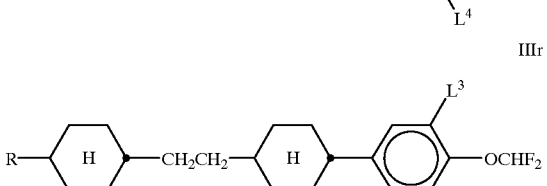
IIIs

-continued

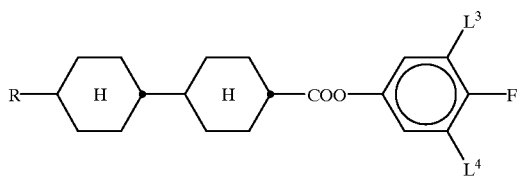
IIIt

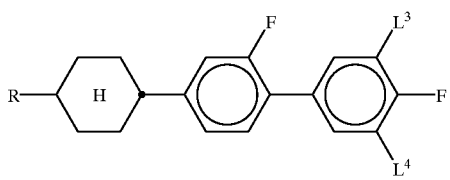
IIIu

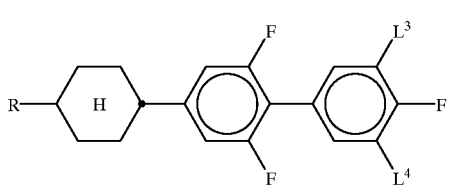
IIIv in which R is as defined under the formula III, and $L^3$ and $L^4$, independently of one another, are each H or F.

Of the compounds of the formulae IIIa to IIIv, particular preference is given to those in which $L^3$ is F, furthermore those in which $L^3$ and $L^4$ are F.

In addition to one or more compounds of the formulae IA and IB, preferred mixtures comprise one, two, three or more compounds of the formulae IIa, IIb, IIc, IIf, IIIb, IIId, IIIf, IIIh, IIIi, IIIs or IIIu, preferably one or more compounds of the formula IIIb, IIId, IIIh or IIIu, and from one to four compounds of the formulae IA and IB and from one to four compounds of the formulae IIa, IIb and/or IIc.

In the preferred compounds of the subformulae to the formulae II and III mentioned above and below, R, $R^1$ and $R^2$, unless stated otherwise, are preferably .straight-chain alkyl, alkenyl or alkoxy, in particular alkyl, having 1 to 12 carbon atoms, in particular having 1 to 7 carbon atoms.

Preference is furthermore given to mixtures which comprise one or more compounds of the subformula IIIb1

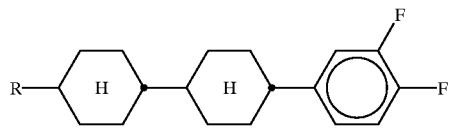
IIIb1 in which R is as defined in the formula III and is preferably alkyl having 1 to 7 carbon atoms or alkenyl having 2 to 7 carbon atoms, in particular vinyl or 1E- or 3E-alkenyl having 3 to 7 carbon atoms.

In the compounds of the formula IIIb1, R is particularly preferably vinyl, 1E-propenyl, 1E-butenyl, 3 -butenyl, 3E-pentenyl, in particular vinyl.

The individual compounds, for example of the formulae II and III or their subformulae, or alternatively other compounds which can be used in the SLCDs according to the invention, are either known or can be prepared analogously to known compounds.

Preferred liquid-crystal mixtures comprise one or more compounds of component B, preferably from 30 to 75%.

The compounds of component B are distinguished, in particular, by their low rotational viscosity values $\gamma_1$.

Component B preferably, in addition to one or more compounds of the formula IB, comprises one or more compounds selected from the group consisting of the compounds of the formulae IV1 to IV9:

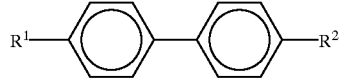
IV1

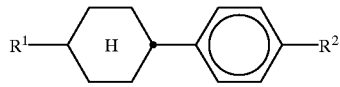
IV2

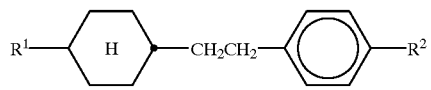
IV3

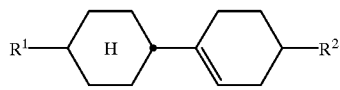
IV4

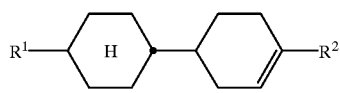
IV5

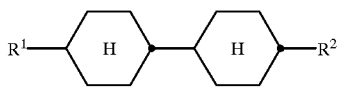
IV6

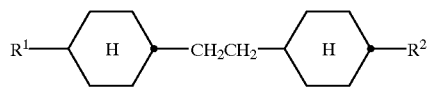
IV7

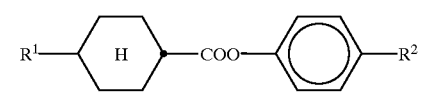
IV8

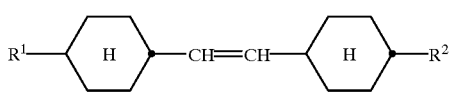
IV9 in which $R^1$ and $R^2$ are each, independently of one another, as defined for R in the formulae II and III, and where the compounds of the formula IV6 are different from the compounds of the formula IB.

Component B preferably additionally comprises one or more compounds selected from the group consisting of the compounds of the formulae IV10 to IV24:

IV10

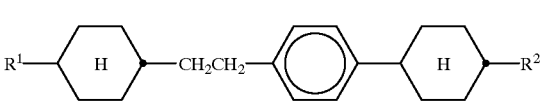
IV11

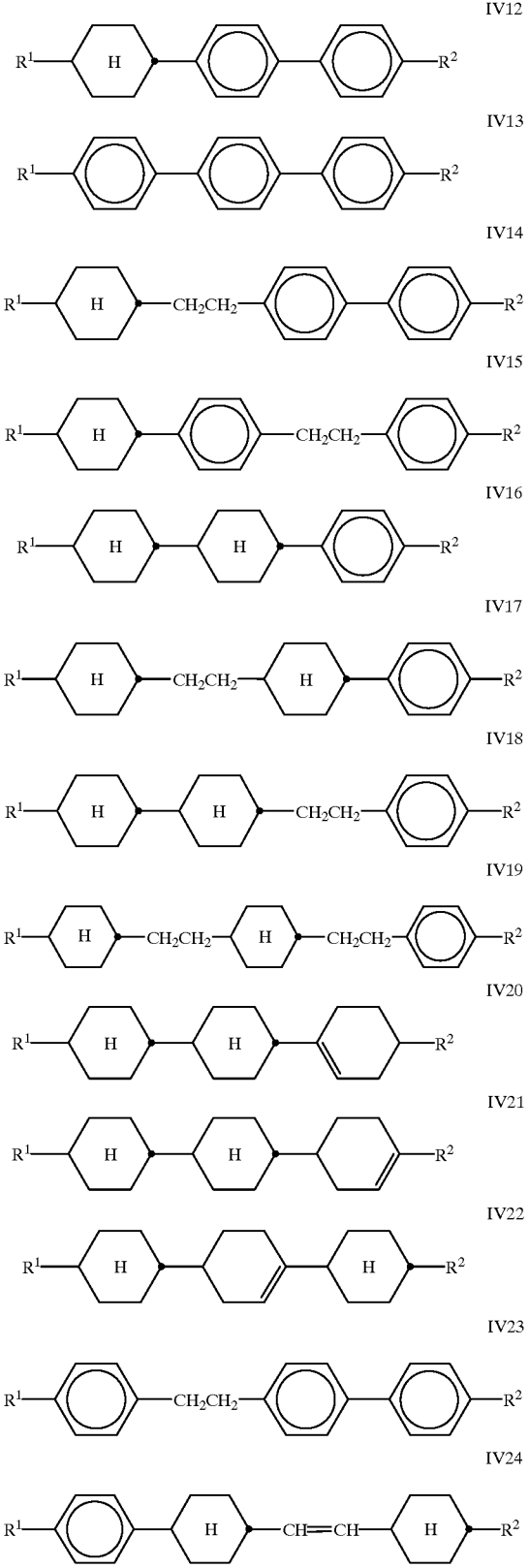

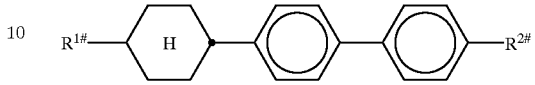

compounds of the formula IB. The 1,4-phenylene groups in IV10 to IV19, IV23 and IV24 may each, independently of one another, also be monosubstituted or polysubstituted by fluorine.

Particular preference is given to mixtures comprising one or more compounds of the formula IV12a:

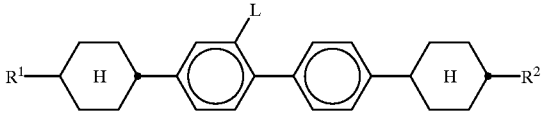

in which $R^{1\#}$ is as defined for $R^3$ in the formula IB, and $R^{2\#}$, is straight-chain alkyl having 1 to 4 carbon atoms.

In these compounds, $R^{1\#}$ is particularly preferably vinyl, 1E-propenyl, 1-butenyl, 2E-butenyl, 3-butenyl, 2E-pentenyl or 3E-pentenyl, $R^{2\#}$ is particularly preferably methyl, ethyl or propyl, in particular methyl or ethyl.

Preference is furthermore given to mixtures comprising compounds of the formual IV12a and compounds of the formulae IB2-1 and/or IB2-2 in which $R^{3a}$ is H, $CH_3$, $C_2H_5$ or n-$C_3H_7$ and $R^{4b}$ is n-alkyl, having 1 to 8 carbon atoms.

Component B preferably additionally, in addition to component IB, comprises one or more compounds selected from the group consisting of the compounds of the formulae IV25 to IV31:

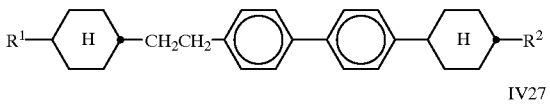

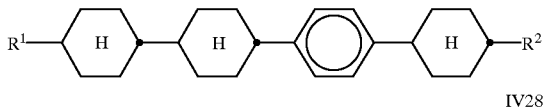

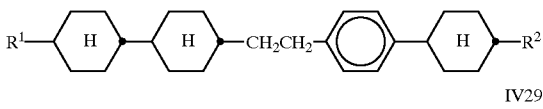

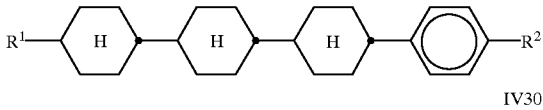

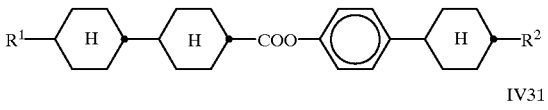

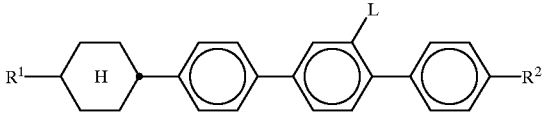

in which $R^1$ and $R^2$ are each, independently of one another, as defined for R in the formulae II and III, and where the compounds of the formula IV16 are different from the in which $R^1$ and $R^2$ are as defined for R in the formulae II and III, and L is F or H. The 1,4-phenylene groups in IV25 to IV31 may also each, independently of one another, be monosubstituted or polysubstituted by fluorine.

Particular preference is given to compounds of the formulae IV25 to IV31 in which $R^1$ is alkyl and $R^2$ is alkyl or alkoxy, in particular alkoxy, in each case having 1 to 7 carbon atoms. Preference is furthermore given to compounds of the formulae IV25 and IV31, in which L is F.

In the compounds of the formulae IV1 to IV31, $R^1$ and $R^2$ are each, independently of one another, particularly preferably straight-chain alkyl or alkoxy having 1 to 12 carbon atoms.

Component B optionally comprises one or more compounds selected from the group consisting of the compounds of the formulae VI and VII:

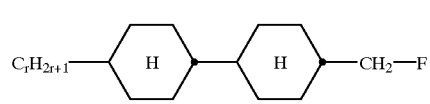

VI

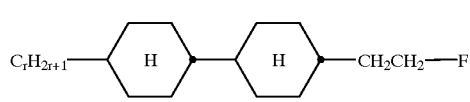

VII in which $C_rH_{2r+1}$ is a straight-chain alkyl group, and r is from 1 to 9.

In a further preferred embodiment, the liquid-crystalline mixtures additionally comprise one or more compounds from the group of compounds of the formulae VIII and IX

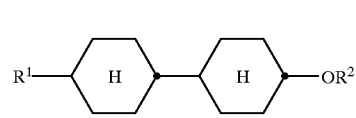

VIII

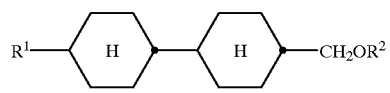

IX in which $R^1$ and $R^2$ are each, independently of one another as defined for R in the formula II and III, and where the compound of the formulae VIII and IX are different from the componds of the formula IB.

Furthermore preferred liquid-crystal mixtures comprise at least one component selected from the group consisting of the compounds of the formulae X to XIV:

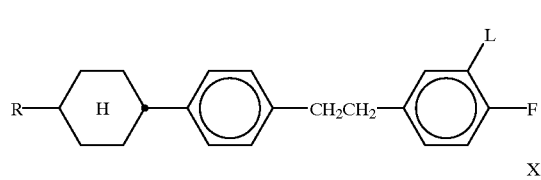

X

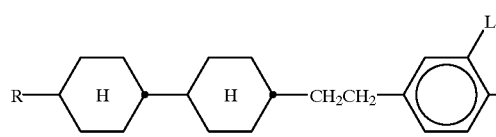

XI

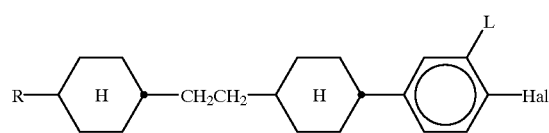

XII

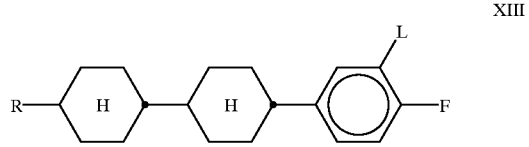

XIII

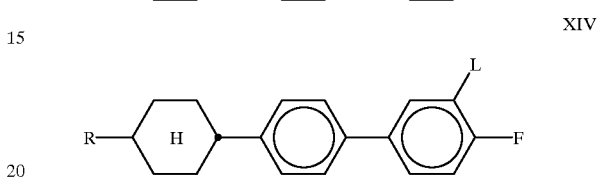

XIV in which Hal is F or Cl, L is H or F, and R is as defined under the formulae II and III, in particular R is alkyl having 1 to 12 carbon atoms.

The liquid-crystal mixtures optionally comprise an optically active component C in such an amount that the ratio between the layer thickness (separation of the outer plates) and the natural pitch of the chiral nematic liquid-crystal mixture is greater than 0.2. For the component, a multiplicity of chiral dopants, some commercially available, is available to the person skilled in the art, for example such as cholesteryl nonanoate, S-811 from Merck KGaA, Darmstadt, FRG, and CB 15 (BDH, Poole, UK). The choice of dopants is not crucial per se.

The proportion of the compounds of component C is preferably from 0 to 10%, in particular from 0 to 5%, particularly preferably from 0 to 3%.

In a particularly preferred embodiment, the mixtures according to the invention comprise from about 5 to 35%, in particular from 5 to 25%, of liquid-crystalline tolan compounds. This enables smaller layer thicknesses to be used, significantly shortening the response times. Besides the tolan compounds of the formula IA, the liquid-crystal mixtures preferably additionally comprise one or more further tolan compounds, preferably selected from group T consisting of the compounds of the formulae T1 to T4:

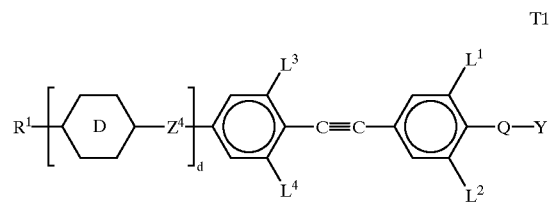

T1

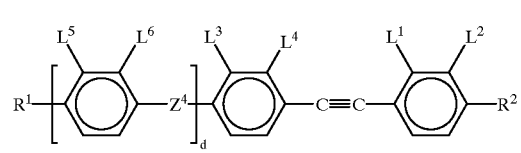

T2

-continued

T3
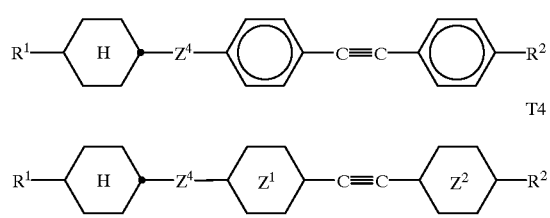

T4 in which

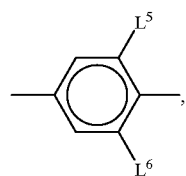 is 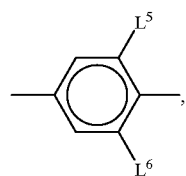 or

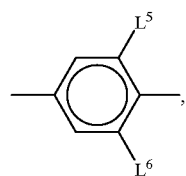, one of the radicals

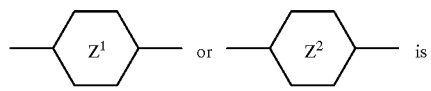 or 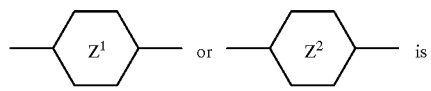 is

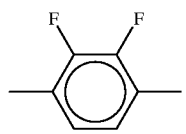

and the other of the radicals

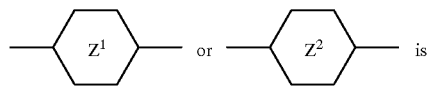 or 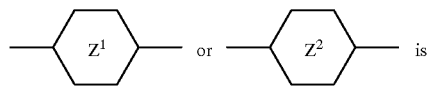 is

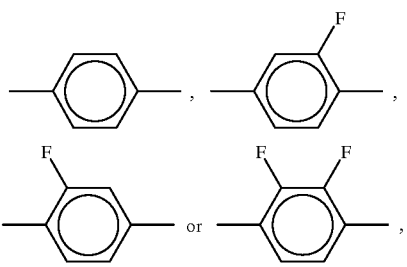, d is 0 or 1,
$L^1$ to $L^6$ are each, independently of one another, H or F,
Q is $-CF_2-$, $-CHF-$, $-CH_2-$, $-OCF_2-$, $-OCHF-$ or a single bond,
Y is F or Cl,
$Z^4$ is $-CO-O-$, $-CH_2CH_2-$ or a single bond, and
$R^1$ and $R^2$ are each, independently of one another, as defined for R in the formulae II and III.

Preferred compounds of the formula T1 conform to the subformulae T1a and T1b

T1a
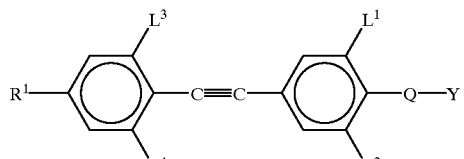

T1b
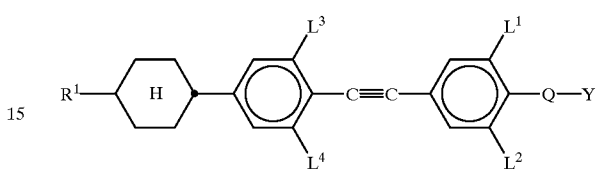

in which $R^1$ is as defined for R in the formulae II and III, $L^1$ to $L^4$ are each, independently of one another, H or F, and Q-Y is F, Cl or $OCF_3$, in particular F or $OCF_3$.

Preferred compounds of the formulae T2 to T4 conform to the subformulae T2a, T2b, T2c, T3a, T3b, T3c and T4a T2a
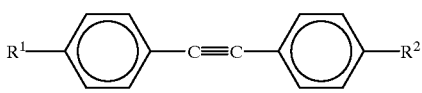

T2b
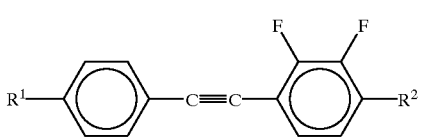

T2c
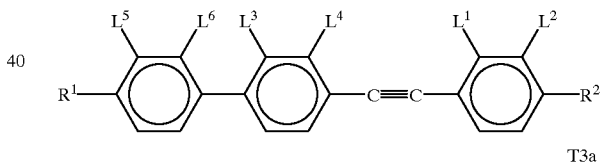

T3a
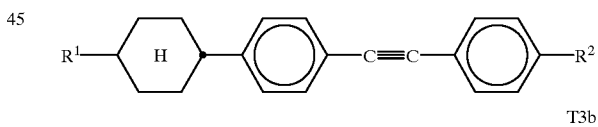

T3b
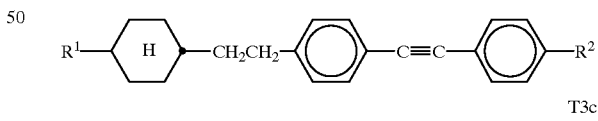

T3c
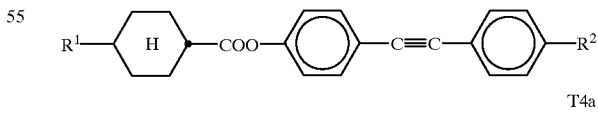

T4a
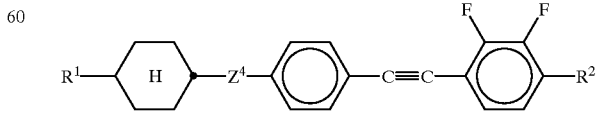

in which $R^1$ and $R^2$ are each, independently of one another, as defined for R in the formulae II and III, $Z^4$ is $-COO-$, —CH$_2$CH$_2$— or a single bond, and L$^1$ to L$^6$ are each, independently of one another, H or F.

Preferred compounds of the formulae T2a to T4a are those of the formulae T2a, T2c, T3a, T3b and T3c. Particularly preferred compounds of the formula T2c are those in which one, two or three of the radicals L$^1$ to L$^6$ are F and the others are H, where L$^1$ and L$^2$ or L$^3$ and L$^4$ or L$^5$ and L$^6$ are not both simultaneously F.

The proportion of compounds from the group T is preferably from 0 to 30%, particularly preferably from 5 to 30%, especially preferably from 5 to 25%.

In a further particularly preferred embodiment, the mixtures according to the invention preferably comprise from about 5 to 20% of one or more compounds having a dielectric anisotropy Δ∈ of less than −1.5 (component D).

Component D preferably comprises one or more compounds containing the structural unit 2,3-difluoro-1,4-phenylene, for example compounds as described in DE-A 38 07 801, 38 07 861, 38 07 863, 38 07 864 or 38 07 908. Particular preference is given to tolans containing this structural unit, as described in International Patent Application PCT/DE 88/00133, in particular those of the formulae T2b and T4a.

Further known compounds of component D are, for example, derivatives of 2,3-dicyanohydroquinones or cyclohexane derivatives containing the structural unit

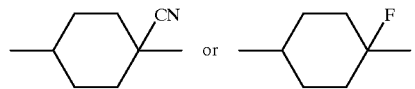

as described in DE-A 32 31 707 or DE-A 34 07 013 respectively.

The liquid-crystal mixture according to the invention preferably comprises one or more compounds selected from group B1 consisting of compounds of the formulae B1I to B1IV:

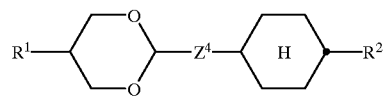

B1I

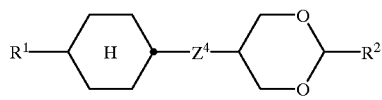

B1II

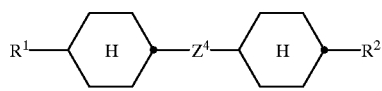

B1III

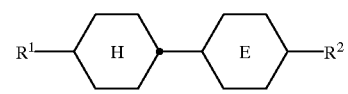

B1IV in which R$^1$ and R$^2$ are each, independently of one another, as defined for R in the formulae II and III, Z$^4$ is —COO—, —CH$_2$CH$_2$— or a single bond, and

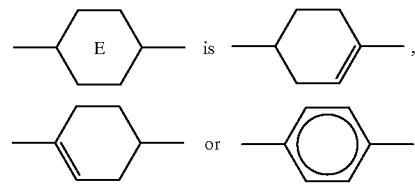

and where the compounds of the formula B1III are different from the compounds of the formula IB, and/or at least one compound selected from group B2 consisting of compounds of the formulae B2I to B2III:

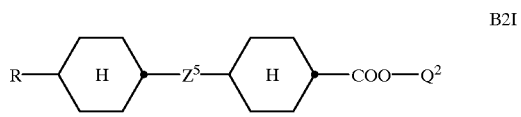

B2I

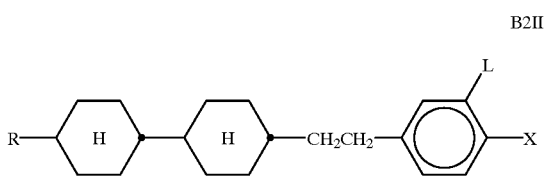

B2II

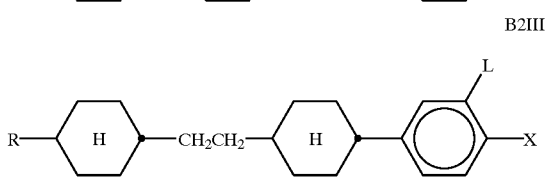

B2III in which

R is as defined under the formulae II and III,
Z$^5$ is —CH$_2$CH$_2$—, —CO—O— or a single bond,
Q2 is

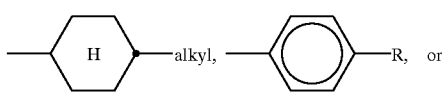

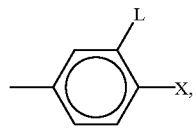

alkyl is an alkyl group having 1 to 9 carbon atoms,
X is CN or F, and
L is H or F, and/or at least one compound selected from group B3 consisting of compounds of the formulae B3I to B3III:

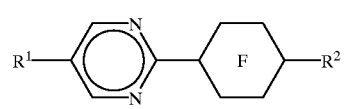

B3I

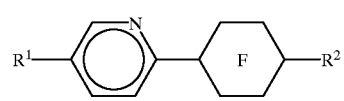

B3II

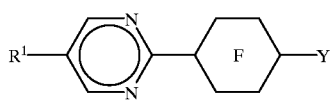

in which
R¹ and R² are each, independently of one another, as defined for R in the formulae II and III,
Y is F or Cl, and

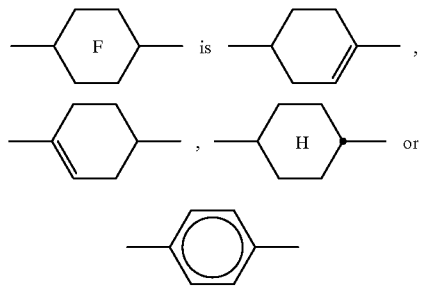

The proportion of the compounds from group B1 is preferably from 10 to 50%, in particular from 15 to 40%. Compounds of the formulae B1III and B1IV are preferred.

Particularly preferred compounds of group B1 are those of the following subformulae:

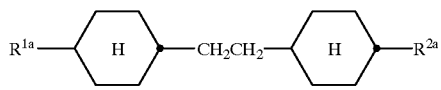

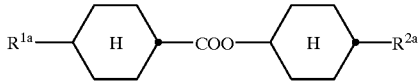

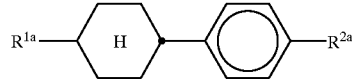

in which
R$^{1a}$ is CH$_3$—(CH$_2$)$_p$—, CH$_3$—(CH$_2$)$_p$—O—, CH$_3$—(CH$_2$)$_p$—O—CH$_2$—, trans-H—(CH$_2$)$_q$—CH=CH—(CH$_2$CH$_2$)$_s$— or trans-H—(CH$_2$)$_q$—CH=CH—(CH$_2$CH$_2$)$_s$—CH$_2$O—,
R$^{2a}$ is CH$_3$—(CH$_2$)$_p$—,
p is 1,2,3 or 4
q is 0,1,2, or 3, and
s is 0 or 1.

The proportion of the compounds of the abovementioned subformulae B1IIIa and B1IIIb together with the compounds of the formula IB1 is preferably from about 5 to 45%, particularly preferably from about 10 to 35%.

The proportion of the compounds of the subformula B1IVa or of the compounds of the formula B1IV is preferably from about 5 to 40%, particularly preferably from about 10 to 35%.

In a particularly preferred embodiment, the mixtures simultaneously comprise compounds of the formulae B1III and B1IV together with the compounds of the formulae IB1 and/or IB2, observing the total proportion for components from group B1.

If compounds of the formulae B1I and/or B1III are present, R¹ and R² are preferably each, independently of one another, n-alkyl having 1 to 7 carbon atoms and, in the case of compounds of the formula B1I, also (trans)-n-alkenyl having 3 to 7 carbon atoms. Z⁴ is preferably a single bond.

Preference is furthermore given to mixtures according to the invention which comprise one or more compounds of the formula B1IV in which

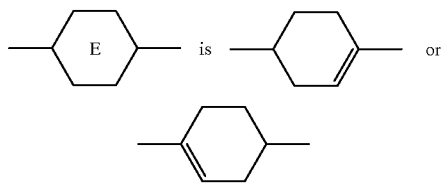

and R¹ and R² each, independently of one another, have one of the preferred meanings indicated above, and are particularly preferably n-alkyl having 1 to 7 carbon atoms.

In all cases, the total proportion of components from group B1 is observed.

The proportion of the compounds from group B2 is preferably from about 5 to 45%, in particular from 5 to 20%. The proportion (preferred ranges) for B2I to B2III is as follows:

B2I: from about 5 to 30%, preferably from about 5 to 15%, sum of B2II and B2III: from about 5 to 25%, preferably from about 10 to 20%.

Preferred compounds from group B2 are shown below:

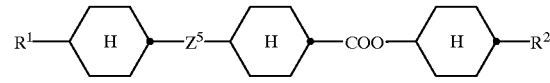

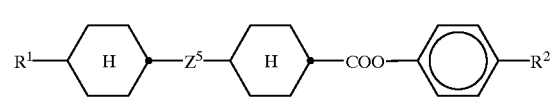

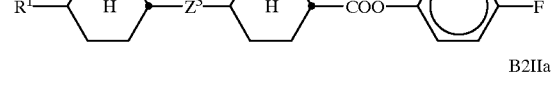

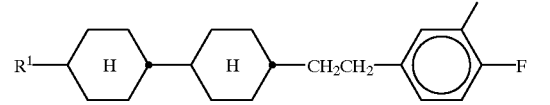

in which R¹ and R² are each, independently of one another, as defined for R in the formulae II and III, L is H or F, and Z⁵ is —CH$_2$CH$_2$—, —COO— or a single bond.

In these compounds, R¹ is preferably n-alkyl having 1 to 7 carbon atoms or (trans)-n-alkenyl having 3 to 7 carbon atoms, $Z^5$ is preferably a single bond, $R^2$ preferably has the preferred meaning given above for R or is fluorine, and L is preferably fluorine.

The mixtures according to the invention preferably comprise one or more compounds selected from the group consisting of B2Ic, B2IIa and B2IIIa in a total proportion of from about 5 to 35%.

In a particularly preferred embodiment, the mixtures according to the invention, in addition to B2Ic, B2IIa and B2IIIa (L=F), comprise further terminally fluorinated compounds, selected, for example, from the group consisting of

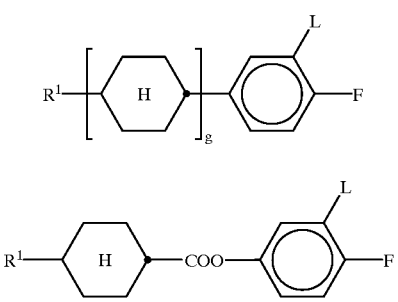

F1

F2 and/or polar heterocyclic compounds selected from the group consisting of

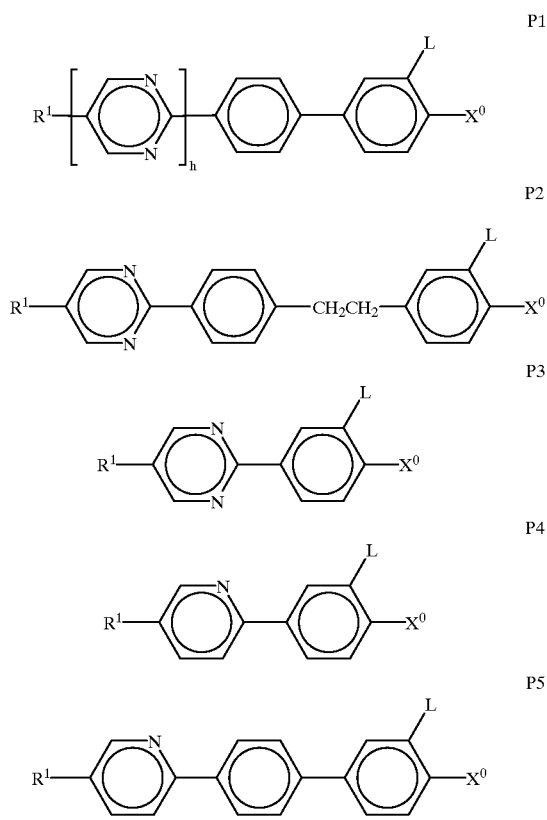

P1

P2

P3

P4

P5 in which $R^1$ is as defined for R in the formulae II and III and is preferably n-alkyl having 1 to 7 carbon atoms or (trans)-n-alkenyl having 3 to 7 carbon atoms, g is 1 or 2, h is 0 or 1, $X^0$ is F, Cl, $CF_3$, —$OCF_3$ or —$OCHF_2$, and L is H or F.

The total proportion of all terminally fluorinated compounds is preferably from about 5 to 65%, in particular from about 15 to 40%.

The proportion of compounds from group B3 is preferably from about 5 to 30%, particularly preferably from about 10 to 20%. $R^1$ is preferably n-alkyl or n-alkoxy, in each case having 1 to 9 carbon atoms.

However, it is also possible to employ analogous compounds containing alkenyl or alkenyloxy groups. Compounds of the formula B3I are preferred.

The terms "alkyl" and "alkoxy" in the definition of $R^a$, $R^b$, R, $R^1$, $R^2$ and $R^4$ embrace straight-chain and branched alkyl and alkoxy groups, in the case of $R^a$, R, $R^1$, $R^2$ and $R^4$ having 1–12, in the case of $R^b$ having 1–5 carbon atoms and especially the straight-chain groups. Particularly preferred alkyl and alkoxy groups are ethyl, propyl, butyl, pentyl, hexyl, heptyl, ethoxy, propoxy, butoxy, pentoxy, hexoxy or heptoxy, and also methyl, octyl, nonyl, decyl, undecyl, dodecyl, methoxy, octoxy, nonoxy, decoxy, undecoxy or dodecoxy.

The term "alkenyl" in the definition of $R^a$, R, $R^1$, $R^2$, $R^3$ and $R^4$ covers straight-chain and branched alkenyl groups, having 2–12 carbon atoms in the case of $R^a$, R, $R^1$, $R^2$ and $R^4$ and having 2–7 carbon atoms in the case of $R^3$, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "alkenyloxy" in the definition of $R^a$ embraces straight-chain and branched alkenyloxy groups having 2–12 carbon atoms, especially the straight-chain groups. In particular it means vinyloxy, propyl-1- or -2-enyloxy, but-1-, -2- or -3-enyloxy, pent-1-, -2-, -3- or -4-enyloxy, hex-1-, -2-, -3-, -4- or -5-enyloxy or hept-1-, -2-, -3-, -4-, -5- or -6-enyloxy, and also oct-1-, -2-, -3-, -4-, -5-, -6- or -7-enyloxy, non-1-, -2-, -3-, -4-, -5-, -6-, -7- or -8-enyloxy, dec-1-, -2-, -3-, -4-, -5-, -6-, -7-, -8-, or -9-enyloxy, undec-1-, -2-, -3-, -4-, -5-, -6-, -7-, -8-, -9- or -10-enyloxy or dodec-1-, -2-, -3-, -4-, -5-, -6-, -7-, -8-, -9-, -10- or -11-enyloxy.

The mixtures according to the invention comprise compounds of the formulae IA and IB and preferably compounds from at least one of groups B1, B2 and B3. They preferably comprise one or more compounds from group B1 and one or more compounds from group B2 and/or B3.

In a preferred embodiment, the liquid-crystalline media according to the invention comprise 3, 4, 5 or 6 compounds of the formulae IA and IB; the content of these compounds is generally from 20 to 70% by weight, preferably from 40 to 70% by weight, based on the total.

In a further preferred embodiment, the mixtures comprise one or more compounds of the following formulae

IV25

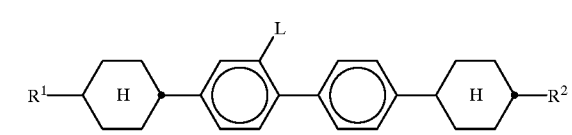

IV30

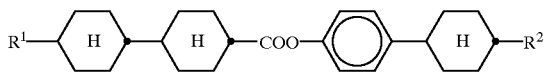

in which R1, R2 and L have the preferred meanings given under compounds of component B. The proportion of these compounds in the liquid-crystal mixtures is preferably from 0 to 45%, in particular from 5 to 30%;

one or more, in particular 1, 2, 3 or 4, compounds selected from the compounds of the formulae IIIb, IIId, IIIf, IIIh, IIIi, IIIs and IIIu;

at least two compounds selected from the compounds of the formulae IIb1, IIb2, IIb3, IIc1 and IIc2. The proportion of these compounds in the liquid-crystal mixtures is preferably from 0 to 60% by weight, particularly from 10 to 45%;

one or more compounds of the formula T1 to T4, in particular one or more compounds of the formula T2a and/or T3a, where the proportion of these compounds in the liquid-crystal mixtures is preferably from 0 to 25%, in particular from 1 to 15%.

Further particularly preferred embodiments relate to liquid-crystal mixtures comprising at least two compounds of the formula AI or AII;

one or more compounds in which R or $R^1$ is a trans-alkenyl group of trans-alkenyloxy group;

one or more compounds selected from the following group:

IV6

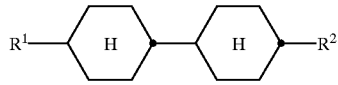

IV12

IV14

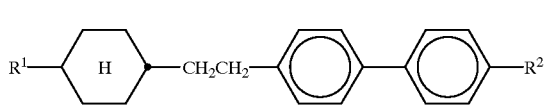

in which $R^1$ and $R^2$ have the preferred meanings given under compounds of component B, and where the compounds of the formula IV6 are different from the compounds of the formula IB. The 1,4-phenylene groups in the abovementioned compounds can also be substituted by fluorine;

one or more compounds of the formulae

IV18

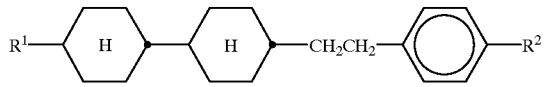

XV

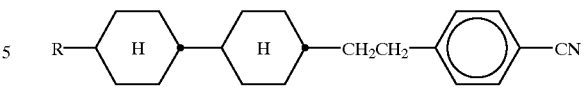

in which R, R1 and R2 are each, independently of one another, as defined for R in the formulae II and III.

In particular when used in SLCDs having high layer thicknesses, the mixtures according to the invention are distinguished by very low overall response times ($t_{tot}=t_{on}+t_{off}$). Low overall response times are an important criterion, in particular, in SLCDs for use as displays in laptops in order to be able to display cursor movements without interference.

The liquid-crystal mixtures used in the STN cells according to the invention are dielectrically positive with $\Delta\epsilon \geq 1$. Particular preference is given to liquid-crystal mixtures where $\Delta\epsilon \geq 3$ and very particularly to those where $\Delta\epsilon \geq 5$.

The liquid-crystal mixtures according to the invention have favourable values for the threshold voltage $V_{10,0,20}$ and for the rotational viscosity γ1. If the value for the optical path difference d. n is specified, the value for the layer thickness d is determined by the optical anisotropy Δn. In particular at relatively high values for d.Δn, the use of liquid-crystal mixtures according to the invention having a relatively high value for the optical anisotropy is generally preferred since the value for d can then be chosen to be relatively small, which results in more favourable values for the response times. However, liquid-crystal displays according to the invention which contain liquid-crystal mixtures according to the invention having relatively small values for Δn are also characterized by advantageous values for the response times.

The liquid-crystal mixtures according to the a invention are furthermore characterized by advantageous values for the steepness of the electrooptical characteristic line and can be operated at high multiplex rates, in particular at temperatures above 20° C. In addition, the liquid-crystal mixtures according to the invention have high stability and favourable values for the electrical resistance and the frequency dependence of the threshold voltage. The liquid-crystal displays according to the invention have a broad operating temperature range and good angle dependence of the contrast.

The construction of the liquid-crystal display elements according to the invention from polarizers, electrode baseplates and electrodes with a surface treatment such that the preferential alignment (director) of the liquid-crystal molecules in each case adjacent thereto is usually twisted by a value of from 160° to 720° from one electrode to the next, corresponds to the structure which is conventional for display elements of this type. The term conventional structure here is broadly drawn and also includes all derivatives and modifications of the STN cell, in particular also matrix display elements, and display elements which contain additional magnets.

The surface tilt angle at the two outer plates may be identical or different. Identical tilt angles are preferred. In STN displays, the pretilt angle is from 1° to 30°, preferably from 1° to 12°, in particular from 3° to 10°.

The twist angle of the STN mixture in the display from alignment layer to alignment layer has a value of between 100° and 600°, preferably between 170° and 300°, in particular between 180° and 270°.

The liquid-crystal mixtures which can be used according to the invention are prepared in a manner which is known per se. In general, the desired amount of the components used in a lesser amount is dissolved in the components making up the principal constituent, expediently at elevated temperature. It is also possible to mix solutions of the components in an organic solvent, for example in acetone, chloroform or methanol, and, after mixing, to remove the solvent again, for example by distillation.

The dielectrics may also contain further additives which are known to a person skilled in the art and are described in the literature. For example, 0–15% of pleochroic dyes may be added.

In the present application and in the examples below, the structures of the liquid-crystal compounds are indicated by acronyms, the transformation into chemical formulae taking place in accordance with tables A and B below. All radicals $C_nH_{2n+1}$ and $C_mH_{2m+1}$ are straight-chain alkyl radicals having n and m carbon atoms respectively. The alkenyl radicals have the trans-configuration. The coding in Table B is self-evident. In Table A, only the acronym for the parent structure is given. In individual cases, the acronym for the parent structure is followed, separated by a dash, by a code for the substituents $R_1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | H | F |
| nN.F.F | $C_nH_{2n+1}$ | CN | H | F | F |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | H | F |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| n-Am | $C_nH_{2n+1}$ | —C≡C—$C_mH_{2m+1}$ | H | H | H |
| n-Vm | $C_nH_{2n+1}$ | —CH=CH—$C_mH_{2m+1}$ | H | H | H |
| nV-Vm | $C_nH_{2n+1}$—CH=CH— | —CH=CH—$C_mH_{2m+1}$ | H | H | H |

The STN displays preferably contain liquid-crystalline mixtures composed of one or more compounds from Tables A and B.

TABL A ($L^1$, $L^2$, $L^3$; each independently of one another, H or F)

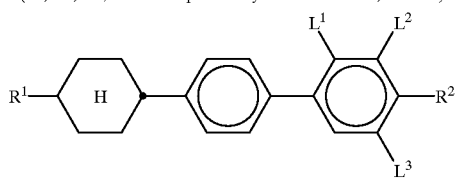

BCH

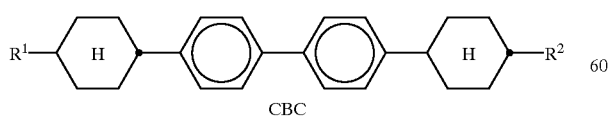

CBC

TABL A-continued

CCH

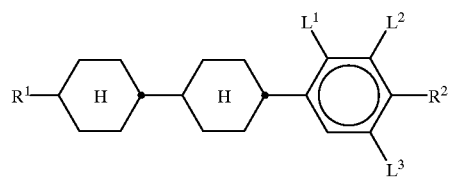

CCP

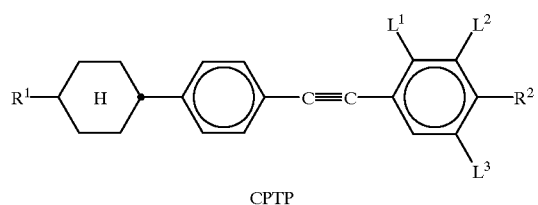

CPTP

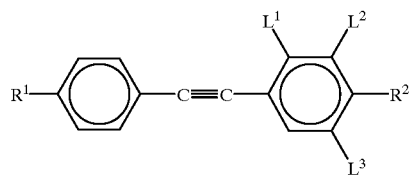

PTP

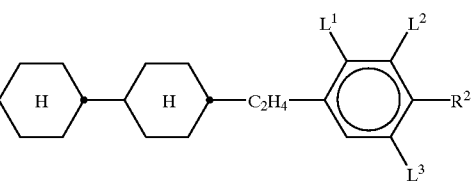

ECCP

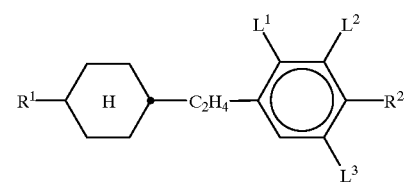

EPCH

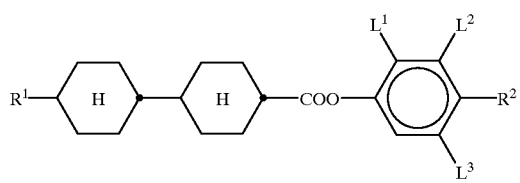

CP

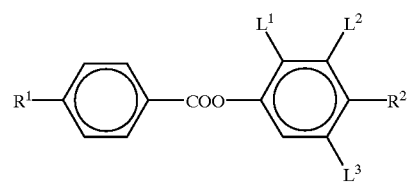

ME

TABLE A-continued

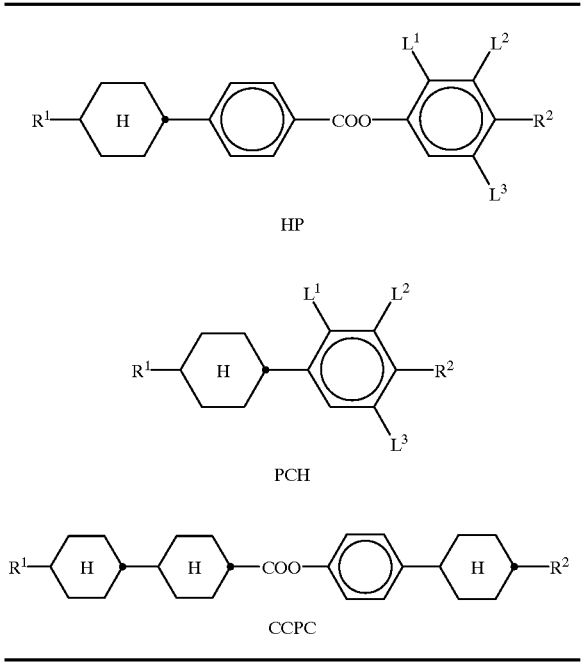

HP

PCH

CCPC

TABLE B

Inm

K3n

CCP-nV-m

CCG-V-F

CBC-nmF

CC-n-V

TABLE B-continued

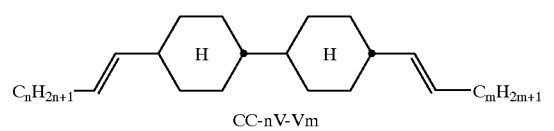
CC-nV-Vm

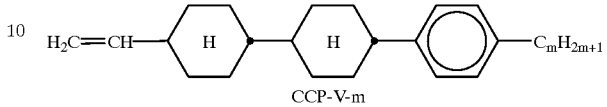
CCP-V-m

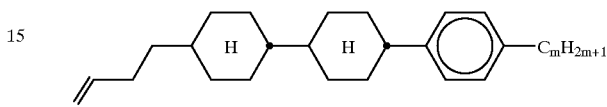
CCP-V2-m

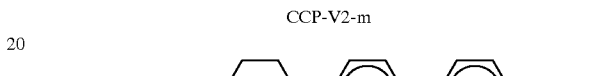
CPP-nV2-m

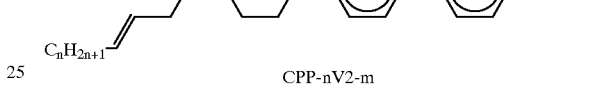
CUTP-nm

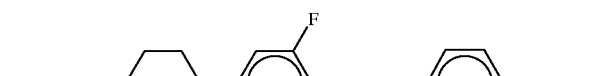
CPTUI-nm

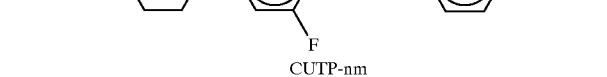
CUTUI-nm

CPTGI-V-m

The entire disclosure of all applications, patents and publications, cited above and below, and of corresponding German Application No. 197 52 951.8, filed Nov. 28, 1997 is hereby incorporated by reference.

EXAMPLES

The examples below are intended to illustrate the invention without representing a limitation.

The following abbreviations are used:

| | |
|---|---|
| S-N | smectic-nematic phase transition temperature |
| N-I | nematic-isotropic phase transition temperature |
| c.p. | clearing point |
| visc. | rotational viscosity (mPa·s) |
| Δn | optical anisotropy (589 nm, 20° C.) |
| $t_{on}$ | time from switching on until 90% of the maximum contrast is achieved |
| $t_{off}$ | time from switching off until 10% of the maximum contrast is achieved |
| steepness | $((V_{90}/V_{10}) \cdot 100\%)$ |
| $V_{10}$ | threshold voldage = characteristic voltage at a contrast of 10% (also written for short as $V_{(10,0,20)}$) |
| $V_{90}$ | characteristic voltage at a contrast of 90% |
| p | pitch |
| $V_{op}$ | operating voltage |
| $t_{ave}$ | $\frac{t_{on} + t_{off}}{2}$ (average response time). |

Above and below, all temperatures are given in ° C. Percentatges are percent by weight. the values for the response times and viscosities relate to 20° C., unless stated otherwise. The response time is, unless stated otherwise, the average value $t_{ave}$ of the switch-on and switch-off times.

The SLCD is, unless stated otherwise, addressed in multiplex operation (multiplex ratio 1:240, bias 1:16).

| Mixture examples | | | |
|---|---|---|---|
| Example A | | | |
| PCH-2 | 10.0% | Clearing point [° C.]: | +103 |
| ME2N.F | 3.0% | Δε [1 kHz, 20° C.]: | +7.6 |
| ME3N.F | 3.0% | Δn [589 nm, 20° C.]: | +0.1228 |
| ME4N.F | 5.0% | STN 240° | |
| CC-5-V | 20.0% | d · Δn [μm]: | 0.85 |
| CCP-V-1 | 15.0% | $V_{(10,0,20)}$ [V]: | 2.35 |
| CCP-V2-1 | 15.0% | Steepness [%]: | 4.6 |
| CCG-V-F | 10.0% | $t_{ave}$ [ms]: | 282 |
| CPP-1V2-2 | 10.0% | d/p: | 0.53 |
| CUTP-31 | 9.0% | | |
| Example B | | | |
| PCH-2 | 10.0% | Clearing point [° C.]: | +102 |
| ME2N.F | 3.0% | Δε [1 kHz, 20° C.]: | +7.4 |
| ME3N.F | 3.0% | Δn [589 nm, 20° C.]: | +0.1221 |
| ME4N.F | 5.0% | STN 240° | |
| CC-5-V | 20.0% | d · Δn [μm]: | 0.85 |
| CCP-V-1 | 15.0% | $V_{(10,0,20)}$ [V]: | 2.36 |
| CCP-V2-1 | 15.0% | Steepness [%]: | 5.5 |
| CCG-V-F | 10.0% | $t_{ave}$ [ms]: | 279 |
| CPP-1V2-2 | 10.0% | d/p: | 0.53 |
| CPTGI-V-4 | 9.0% | | |
| Example C | | | |
| PCH-2 | 10.0% | Clearing point [° C.]: | +103 |
| ME2N.F | 3.0% | Δε [1 kHz, 20° C.]: | +7.4 |
| ME3N.F | 3.0% | Δn [589 nm, 20° C.]: | +0.1233 |
| ME4N.F | 5.0% | STN 240° | |
| CC-5-V | 20.0% | d · Δn [μm]: | 0.85 |
| CCP-V-1 | 15.0% | $V_{(10,0,20)}$ [V]: | 2.34 |
| CCP-V2-1 | 15.0% | Steepness [%]: | 5.4 |
| CCG-V-F | 10.0% | $t_{ave}$ [ms]: | 270 |
| CPP-1V2-2 | 10.0% | d/p: | 0.53 |
| CPTGI-V-2 | 9.00% | | |
| Example D | | | |
| PCH-2 | 10.0% | Clearing point [° C.]: | +103 |
| ME2N.F | 3.0% | Δε [1 kHz, 20° C.]: | +7.6 |
| ME3N.F | 3.0% | Δn [589 nm, 20° C.]: | +0.1222 |
| ME4N.F | 5.0% | STN 240° | |

| -continued | | | |
|---|---|---|---|
| Mixture examples | | | |
| CC-5-V | 20.0% | d · Δn [μm]: | 0.85 |
| CCP-V-1 | 15.0% | $V_{(10,0,20)}$ [V]: | 2.32 |
| CCP-V2-1 | 15.0% | Steepness [%]: | 5.4 |
| CCG-V-F | 10.0% | $t_{ave}$ [ms]: | 296 |
| CPP-1V2-2 | 10.0% | d/p: | 0.53 |
| CPTUI-32 | 9.0% | | |
| Example E | | | |
| PCH-2 | 10.0% | Clearing point [° C.]: | +101 |
| ME2N.F | 3.0% | Δε [1 kHz, 20° C.]: | +7.5 |
| ME3N.F | 3.0% | Δn [589 nm, 20° C.]: | +0.1213 |
| ME4N.F | 5.0% | STN 240° | |
| CC-5-V | 20.0% | d · Δn [μm]: | 0.85 |
| CCP-V-1 | 15.0% | $V_{(10,0,20)}$ [V]: | 2.34 |
| CCP-V2-1 | 15.0% | Steepness [%]: | 5.2 |
| CCG-V-F | 10.0% | $t_{ave}$ [ms]: | 308 |
| CPP-1V2-2 | 10.0% | d/p: | 0.53 |
| CUTUI-32 | 9.0% | | |

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A supertwist liquid-crystal display comprising:

two outer plates which, together with a frame, form a cell, electrode layers with alignment layers on the insides of the outer plates, a pretilt angle between the longitudinal axis of the molecules at the surface of the outer plates and the outer plates of from about 1 degree to 30 degrees, and a twist angle of the liquid-crystal mixture in the cell from alignment layer to alignment layer with a value of between 100° and 600°, and a nematic liquid-crystal mixture of positive dielectric anisotropy which is present in the cell, comprising:
 a) 5–90% by weight of a liquid-crystalline component A consisting of one or more compounds having a dielectric anisotropy of greater than +1.5;
 b) 10–80% by weight of a liquid-crystalline component B consisting of one or more compounds having a dielectric anisotropy of between −1.5 and +1.5;
 c) 0–20% by weight of a liquid-crystalline component D consisting of one or more compounds having a dielectric anisotropy of below −1.5; and
 d) an optically active component C in such an amount that the ratio between the layer thickness and the natural pitch of the chiral nematic liquid-crystal mixture is from about 0.2 to 1.3, wherein the liquid-crystal mixture comprises one or more compounds of the formula IA

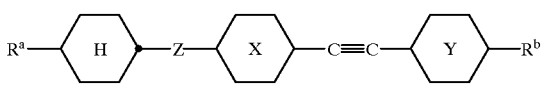

in which
 $R^a$ is alkyl, alkoxy, alkenyl or alkenyloxy having 1 to 12 carbon atoms,
 $R^b$ is alkyl or alkoxy having 1 to 5 carbon atoms, Z is —COO—, —CH$_2$CH$_2$— or a single bond, and

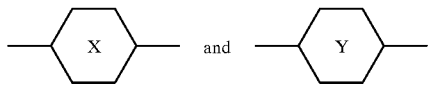

are each, independently of one another,

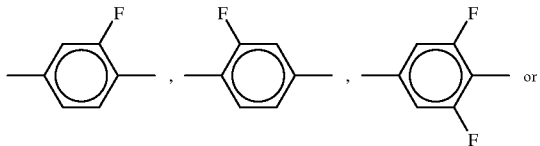

and one of the rings

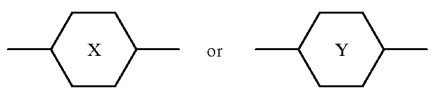

may alternatively be

and component B comprises one or more compounds of the formula IB

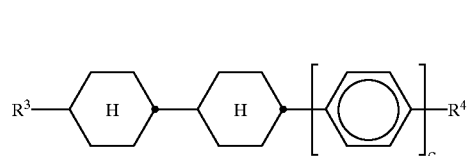

in which
R$^3$ is an alkenyl group having 2 to 7 carbon atoms,
R$^4$ is as defined for R$^a$ in the formula IA, and
c is 0 or 1.

2. A liquid-crystal display according to claim 1, wherein the liquid-crystal mixture comprises one or more compounds selected from the formulae IA1 to IA10

IA1
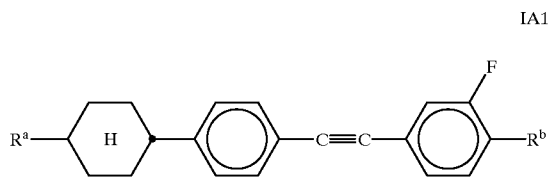

IA2
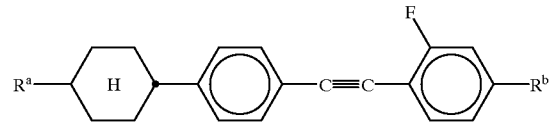

IA3
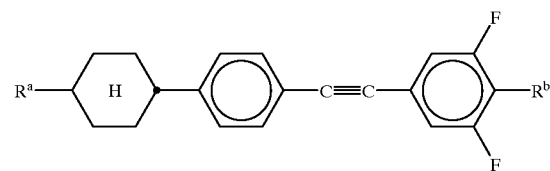

IA4
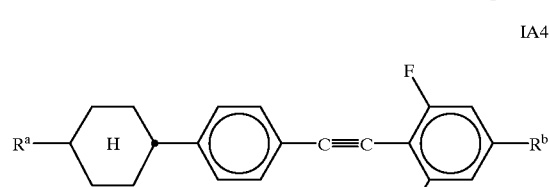

IA5

IA6
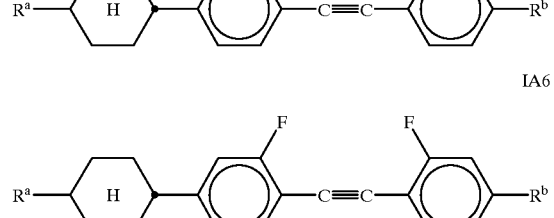

IA7
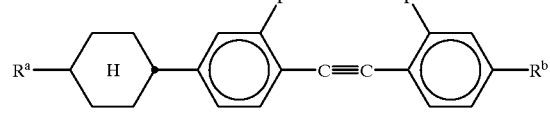

IA8
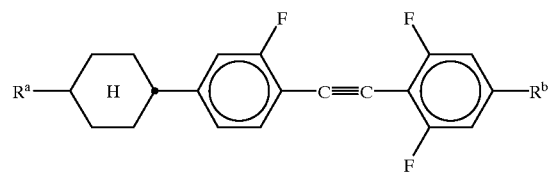

IA9
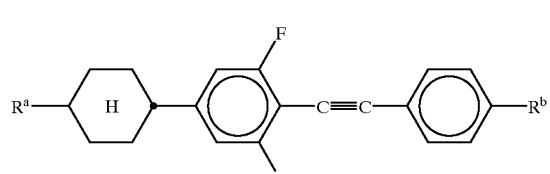

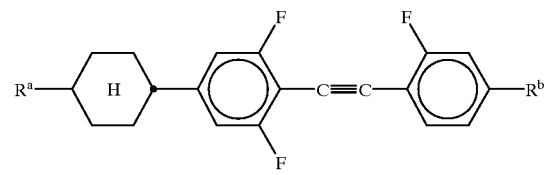

-continued

IA10

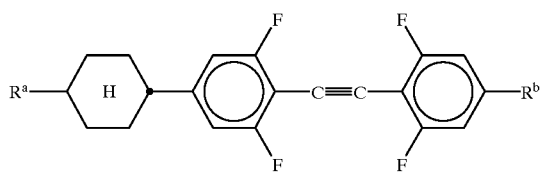

in which
R$^a$ is straight-chain alkyl having 1 to 5 carbon atoms, vinyl or straight-chain 1E- or 3E-alkenyl having 3 to 7 carbon atoms, and
R$^b$ is straight-chain alkyl having 1 to 5 carbon atoms.

3. A liquid-crystal display according to claim 1, wherein component B comprises one or more of the following compounds

IB1

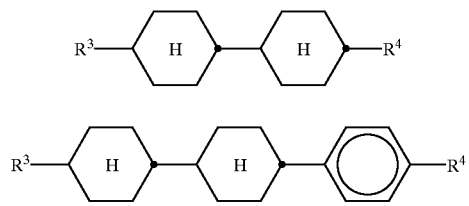

IB2 in which R$^3$ is vinyl or 1E-alkenyl or 3E-alkenyl having 3 to 7 carbon atoms and R$^4$ is as defined in claim 1 for R$^a$.

4. A liquid-crystal display according to claim 1, wherein component B comprises one or more of the following compounds

IB1-1

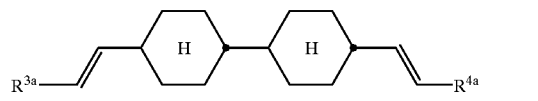

IB1-2

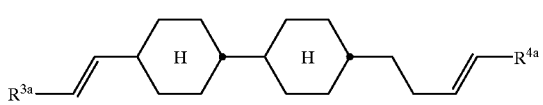

IB1-3

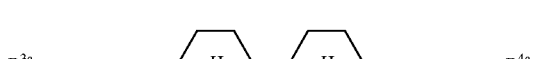

IB1-4

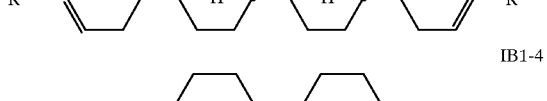

IB1-5

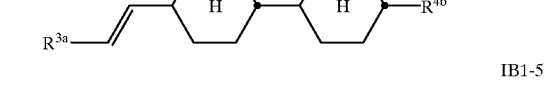

in which R$^{3a}$ and R$^{4a}$ are in each case independently of one another H, CH$_3$, C$_2$H$_5$ or n-C$_3$H$_7$ and R$^{4b}$ is n-alkyl having 1 to 8 carbon atoms.

5. A liquid-crystal display according to claim 1, wherein component B comprises one or more of the following compounds

IB2-1

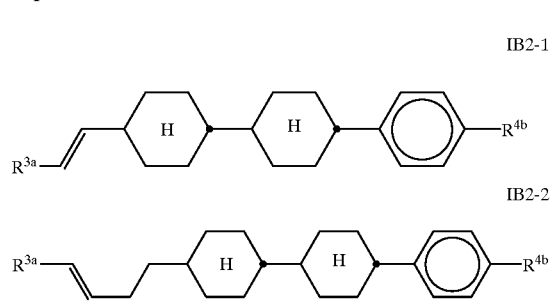

IB2-2 in which R$^{3a}$ is H, CH$_3$, C$_2$H$_5$ or n-C$_3$H$_7$ and R$^{4b}$ is n-alkyl having 1 to 8 carbon atoms.

6. A liquid-crystal display according to claim 1, wherein component A additionally comprises one or more compounds of the formulae II and/or III

II

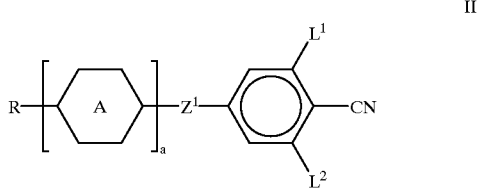

III

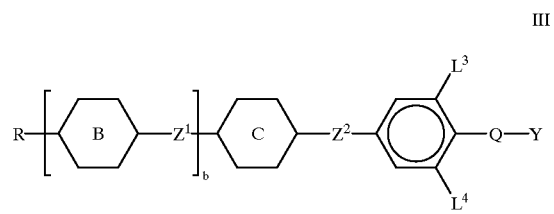

in which

R is an alkyl, alkoxy or alkenyl group having 1 to 12 carbon atoms, in which, one or two non-adjacent CH$_2$ groups are optionally replaced by —O—, —CH=CH—, —CO—, —OCO— or —COO— in such a way that O atoms are not linked directly to one another,

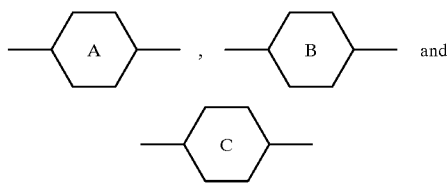 and are each, independently of one another,

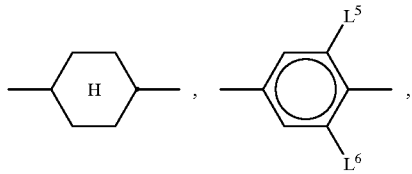

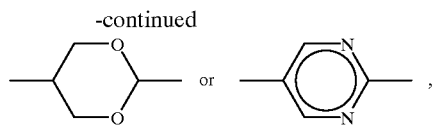

L¹ to L⁶ are each, independently of one another, H or F,

Z¹ is —COO—, —CH₂CH₂— or a single bond,

Z² is —CH₂CH₂—, —COO—, —C≡C— or a single bond,

Q is —CF₂—, —CHF—, —CH₂—, —OCF₂—, —OCHF—, —OCH₂— or a single bond,

Y is F or Cl a is 1 or 2, and b is 0 or 1.

7. A liquid-crystal display according to claim 6, wherein component A comprises at least one compound of the following formulae:

IIa
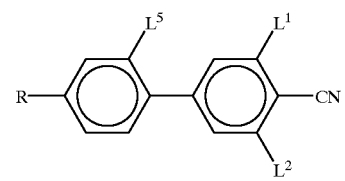

IIb
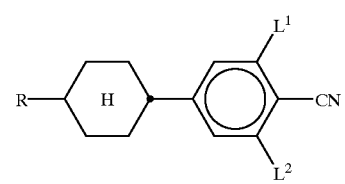

IIc
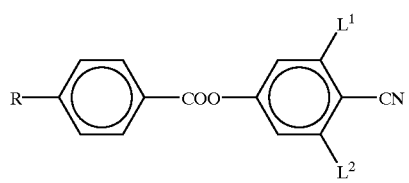

IIf
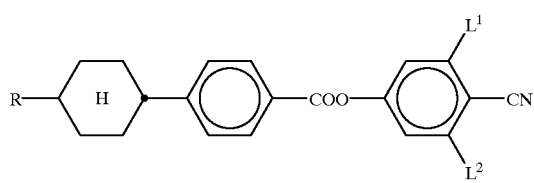

where R, L¹, L² and L⁵ are as defined in claim 6.

8. A liquid-crystal display according to claim 1, wherein component A comprises one or more compounds of the following formula:

IIIb1
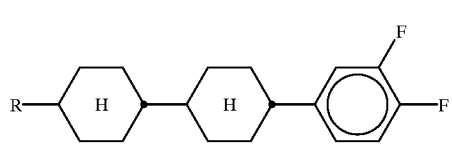

in which R is vinyl or 1E-alkenyl or 3E-alkenyl having 2 to 7 carbon atoms.

9. A liquid-crystal display according to claim 1, wherein the liquid crystal mixture further comprises one or more of the following compounds:

T1a
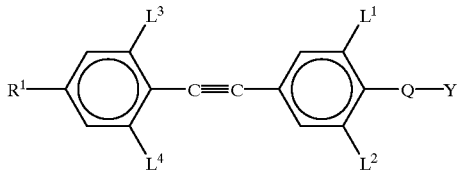

T1b
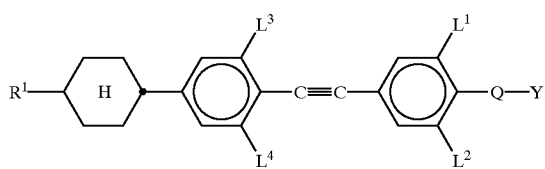

in which R¹ is an alkyl, alkoxy or alkenyl group having 1 to 12 carbon atoms, in which, one or two non-adjacent CH₂ groups are optionally replaced by —O—, —CH=CH—, —CO—, —OCO— or —COO— in such a way that O atoms are not linked directly to one another, L¹ to L⁴ are each, independently of one another, H or F and Q-Y is F, Cl or OCF₃.

10. A liquid-crystal display according to claim 1, wherein the liquid crystal mixture further comprises one or more compounds selected from the group consisting of those of the formulae T2a, T2c, T3a, T3b and T3c:

T2a
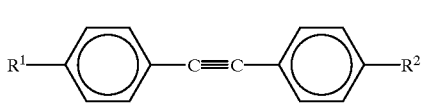

T2c
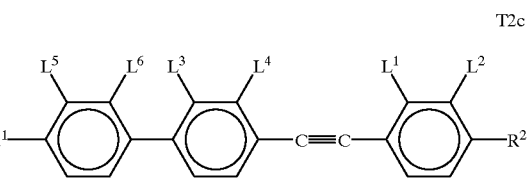

T3a
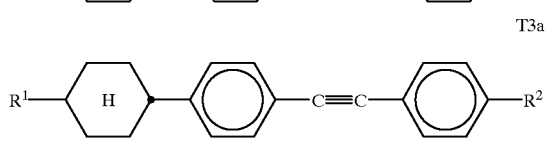

T3b
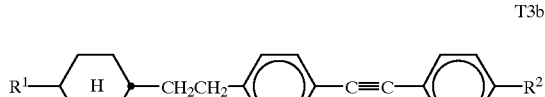

T3c

in which R¹ and R² are each, independently of one another, an alkyl, alkoxy or alkenyl group having 1 to 12 carbon atoms, in which, one or two non-adjacent CH₂ groups are optionally replaced by —O—, —CH=CH—, —CO—, —OCO— or —COO— in such a way that O atoms are not linked directly to one another, and, in the compounds of the formula T2c, one, two or three radicals $L^1$ to $L^6$ are F and the others are H, where $L^1$ and $L^2$ or $L^3$ and $L^4$ or $L^5$ and $L^6$ are not both simultaneously F.

11. A liquid crystal display according to claim 1, wherein component B additionally comprises one or more compounds of the formulae IV1 to IV24:

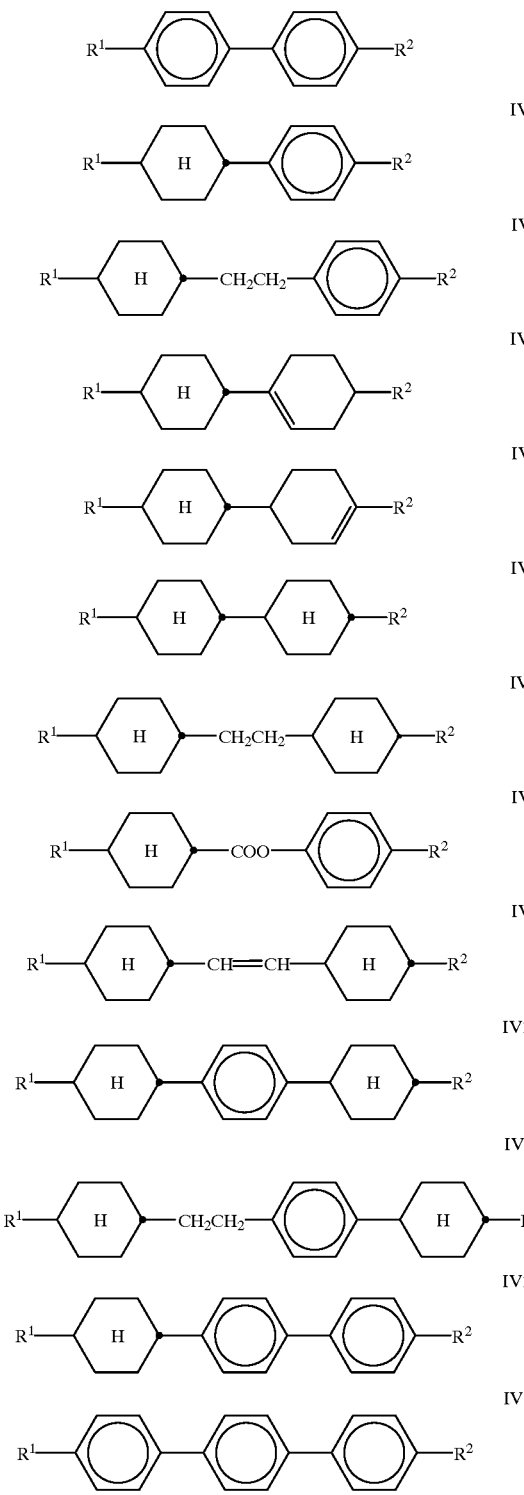

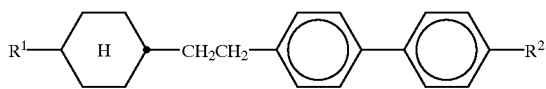

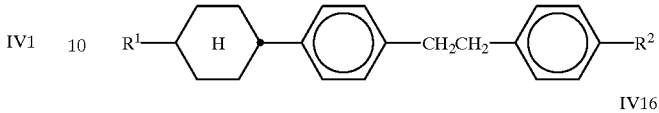

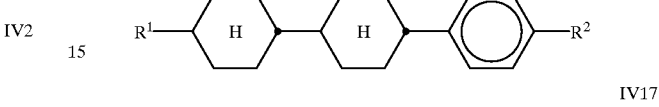

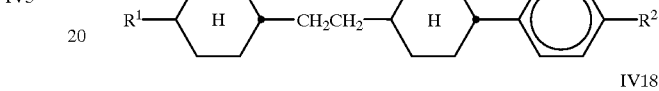

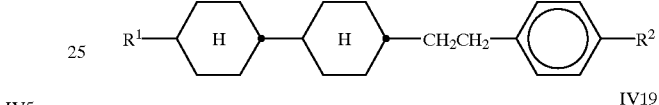

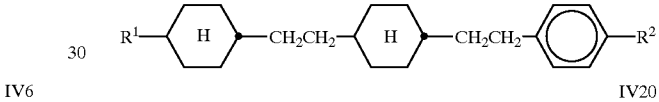

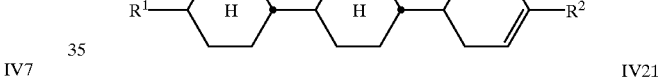

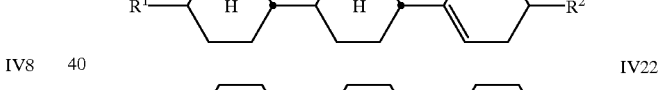

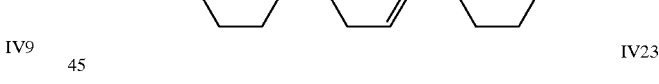

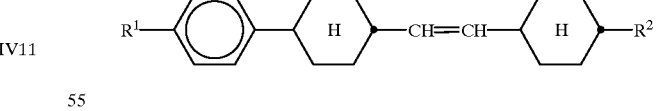

in which $R^1$ and $R^2$ are each, independently of one another, an alkyl, alkoxy or alkenyl group having 1 to 12 carbon atoms, in which, one or two non-adjacent $CH_2$ groups are optionally replaced by —O—, —CH=CH—, —CO—, —OCO— or —COO— in such a way that O atoms are not linked directly to one another, and where the compounds of the formulae IV6 and IV16 are different from the compounds of the formula IB from claim 1.

12. The liquid-crystal display of claim 1, wherein the nematic liquid-crystal mixture comprises at least one compound of the formula IA wherein Z is a single bond.

13. The liquid crystal display of claim 1, wherein the nematic liquid-crystal mixture comprises at least one compound of the formula IA wherein

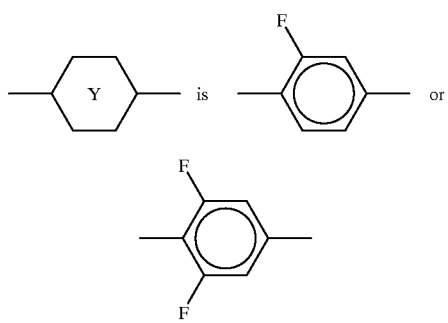

14. The liquid crystal display of claim 1, wherein the nematic liquid-crystal mixture comprises at least one compound of the formula IA wherein

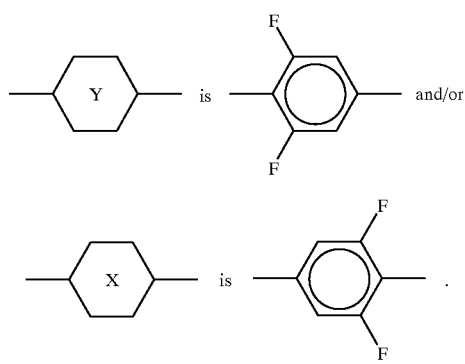

15. The liquid crystal display of claim 1, wherein the nematic liquid-crystal mixture comprises 3–6 compounds of the formulae IA and IB and the content of these compounds is 20 to 70% by weight based on the total weight of the nematic liquid-crystal mixture.

16. The liquid crystal display of claim 1, wherein the pretilt angle is from 1° to 12° and the twist angle is from 170° to 300°.

17. The liquid crystal display of claim 1, wherein the nematic liquid-crystal mixture comprises at least one compound of the formula IA wherein

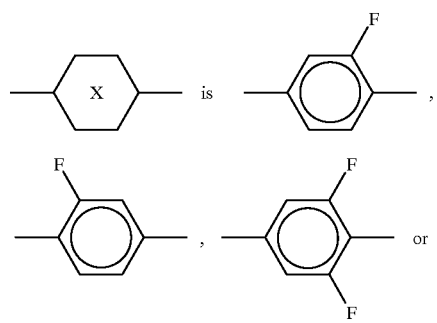

-continued

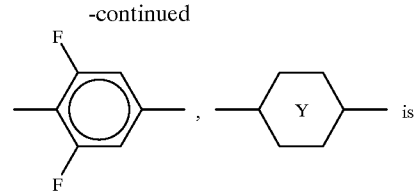

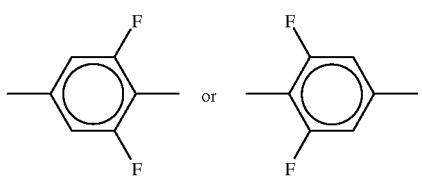

and one of the rings

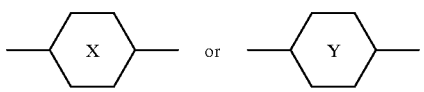

may alternatively be

18. A liquid-crystal mixture comprising:
a) 5–90% by weight of a liquid-crystalline component A consisting of one or more compounds having a dielectric anisotropy of greater than +1.5;
b) 10–80% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5; and
d) an optically active component C in such an amount that the ratio between the layer thickness and the natural pitch of the chiral nematic liquid-crystal mixture is from about 0.2 to 1.3, wherein the liquid-crystal mixture comprises one or more compounds of the formula IA

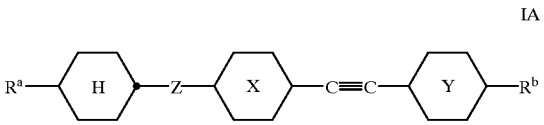

in which
$R^a$ is alkyl, alkoxy, alkenyl or alkenyloxy having 1 to 12 carbon atoms,
$R^b$ is alkyl or alkoxy having 1 to 5 carbon atoms,
Z is —COO—, —CH$_2$CH$_2$— or a single bond, and

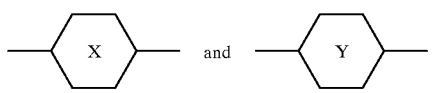

are each, independently of one another,

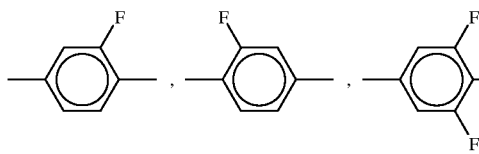

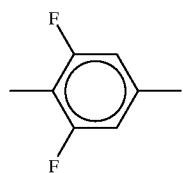

and one of the rings

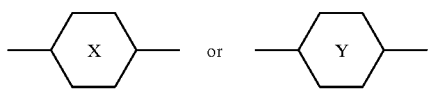

may alternatively be

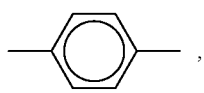

and component B comprises one or more compounds of the formula IB

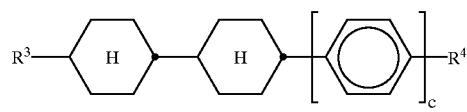

in which
   $R^3$ is an alkenyl group having 2 to 7 carbon atoms,
   $R^4$ is as defined for $R^a$ in the formula IA, and
   c is 0 or 1.
19. A liquid-crystal mixture of claim 18, which comprises at least one compound of formula IA wherein

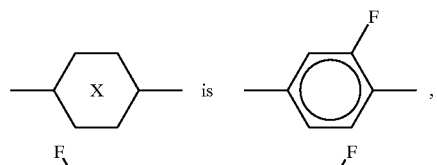

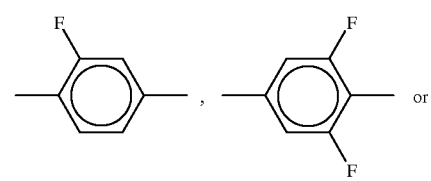

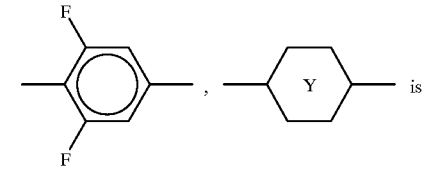

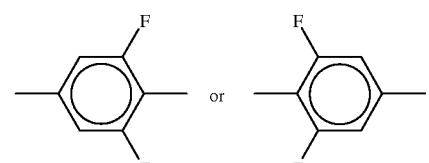

and one of the rings

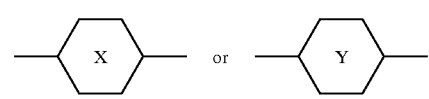

may alternatively be

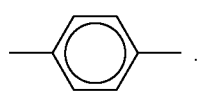

* * * * *